US010085425B2

(12) United States Patent
Funaya et al.

(10) Patent No.: US 10,085,425 B2
(45) Date of Patent: Oct. 2, 2018

(54) ELECTRONIC APPARATUS AND MANUFACTURING METHOD THEREFOR

(71) Applicant: RENESAS ELECTRONICS CORPORATION, Kawasaki-shi (JP)

(72) Inventors: Takuo Funaya, Kawasaki (JP);
Tomohiro Nishiyama, Kawasaki (JP);
Hiroki Shibuya, Kawasaki (JP);
Manabu Okamoto, Kawasaki (JP)

(73) Assignee: RENESAS ELECTRONICS CORPORATION, Tokyo (JP)

( * ) Notice: Subject to any disclaimer, the term of this patent is extended or adjusted under 35 U.S.C. 154(b) by 422 days.

(21) Appl. No.: 14/752,886

(22) Filed: Jun. 27, 2015

(65) Prior Publication Data

US 2016/0000045 A1 Jan. 7, 2016

(30) Foreign Application Priority Data

Jul. 4, 2014 (JP) .................................. 2014-138888

(51) Int. Cl.
*A61N 1/375* (2006.01)
*A01K 29/00* (2006.01)
(Continued)

(52) U.S. Cl.
CPC .......... *A01K 29/005* (2013.01); *A01K 11/006* (2013.01); *A61B 5/0002* (2013.01);
(Continued)

(58) Field of Classification Search
CPC ........ A01K 29/05; A61N 1/372; A61N 1/375; A61B 1/00; A61B 1/05; A61B 1/09;
(Continued)

(56) References Cited

U.S. PATENT DOCUMENTS 4,628,928 A * 12/1986 Lowell ................... A61N 1/375
600/486
4,771,772 A * 9/1988 DeWitt ............. A61M 5/14276
600/488
(Continued)

FOREIGN PATENT DOCUMENTS

JP       H 08-84779 A     4/1996
JP       2000-023924 A    1/2000
(Continued)

OTHER PUBLICATIONS

Japanese Office Action, dated Apr. 24, 2018, in Japanese Application No. 2014-138888 and English Translation thereof.

*Primary Examiner* — Xiaoliang Chen
(74) *Attorney, Agent, or Firm* — McGinn I.P. Law Group, PPLC.

(57) ABSTRACT

An electronic apparatus is provided which, even when the electronic apparatus configuring a node is implanted in the body of an object animal, makes the object animal hard to feel stress and can acquire effective data about the natural behavior and state of the object animal. As shown in FIG. 12, a module unit and a battery are arranged separated from each other. That is, an electronic apparatus according to the present embodiment 1 adopts a case including a first capacity part and a second capacity part both arranged separated from each other to thereby accommodate the module unit in an internal space of the first capacity part and accommodate the battery in an internal space of the second capacity part.

18 Claims, 30 Drawing Sheets

(51) Int. Cl.
*H04W 4/00* (2018.01)
*G01D 11/24* (2006.01)
*H04W 4/70* (2018.01)
*A01K 11/00* (2006.01)
*A61B 5/00* (2006.01)
*A61D 17/00* (2006.01)
*A61B 5/11* (2006.01)

(52) U.S. Cl.
CPC ............... *A61B 5/11* (2013.01); *A61D 17/00* (2013.01); *G01D 11/245* (2013.01); *H04W 4/005* (2013.01); *H04W 4/70* (2018.02)

(58) Field of Classification Search
CPC .. A61B 1/165; A61B 1/29; A61B 1/36; A61B 1/156; A61B 1/158; A61B 18/02; A61B 18/218
USPC .......... 361/814; 250/370.04, 497.1; 600/101, 600/109, 300, 309, 476, 486, 488; 604/140, 141, 151, 266, 500, 892.1; 606/1, 20, 21, 24, 25, 201; 607/36, 37, 607/45
See application file for complete search history.

(56) References Cited

U.S. PATENT DOCUMENTS

| | | | | |
|---|---|---|---|---|
| 5,135,499 | A * | 8/1992 | Tafani | A61M 31/002 604/140 |
| 5,256,878 | A * | 10/1993 | LeVert | G01T 1/24 250/370.04 |
| 6,402,689 | B1 | 6/2002 | Scarantino et al. | |
| 6,498,951 | B1 * | 12/2002 | Larson | A61N 1/375 607/36 |
| 7,095,372 | B2 | 8/2006 | Soler Castany et al. | |
| 7,914,442 | B1 * | 3/2011 | Gazdzinski | A61B 1/00009 600/109 |
| 8,068,897 | B1 * | 11/2011 | Gazdzinski | A61B 1/00016 600/109 |
| 2001/0051766 | A1 * | 12/2001 | Gazdzinski | A61B 1/00016 600/309 |
| 2002/0035385 | A1 * | 3/2002 | Deziz | A61N 1/375 607/37 |
| 2002/0038136 | A1 * | 3/2002 | Zaouali | A61N 1/375 607/36 |
| 2003/0023150 | A1 * | 1/2003 | Yokoi | A61B 1/00016 600/300 |
| 2005/0156207 | A1 | 7/2005 | Yazawa et al. | |
| 2011/0066178 | A1 * | 3/2011 | Blin | A61B 17/1325 606/201 |
| 2011/0163919 | A1 | 7/2011 | Suzuki | |
| 2012/0071710 | A1 * | 3/2012 | Gazdzinski | A61B 1/00016 600/101 |
| 2013/0184694 | A1 * | 7/2013 | Fourkas | A61B 18/02 606/20 |
| 2013/0190745 | A1 * | 7/2013 | Fourkas | A61B 18/02 606/25 |
| 2013/0204317 | A1 * | 8/2013 | Sauter-Starace | A61N 1/36067 607/45 |
| 2014/0276539 | A1 * | 9/2014 | Allison | A61B 18/02 604/500 |
| 2014/0276708 | A1 * | 9/2014 | Karnik | A61B 18/02 606/21 |
| 2014/0343543 | A1 * | 11/2014 | Karnik | A61B 18/02 606/24 |

FOREIGN PATENT DOCUMENTS

| | | |
|---|---|---|
| JP | 2002-525153 A | 8/2002 |
| JP | 2005-207797 A | 8/2005 |
| JP | 2006-505973 A | 2/2006 |
| JP | 2007-313594 A | 12/2007 |
| WO | WO 2010/026990 A1 | 3/2010 |

* cited by examiner

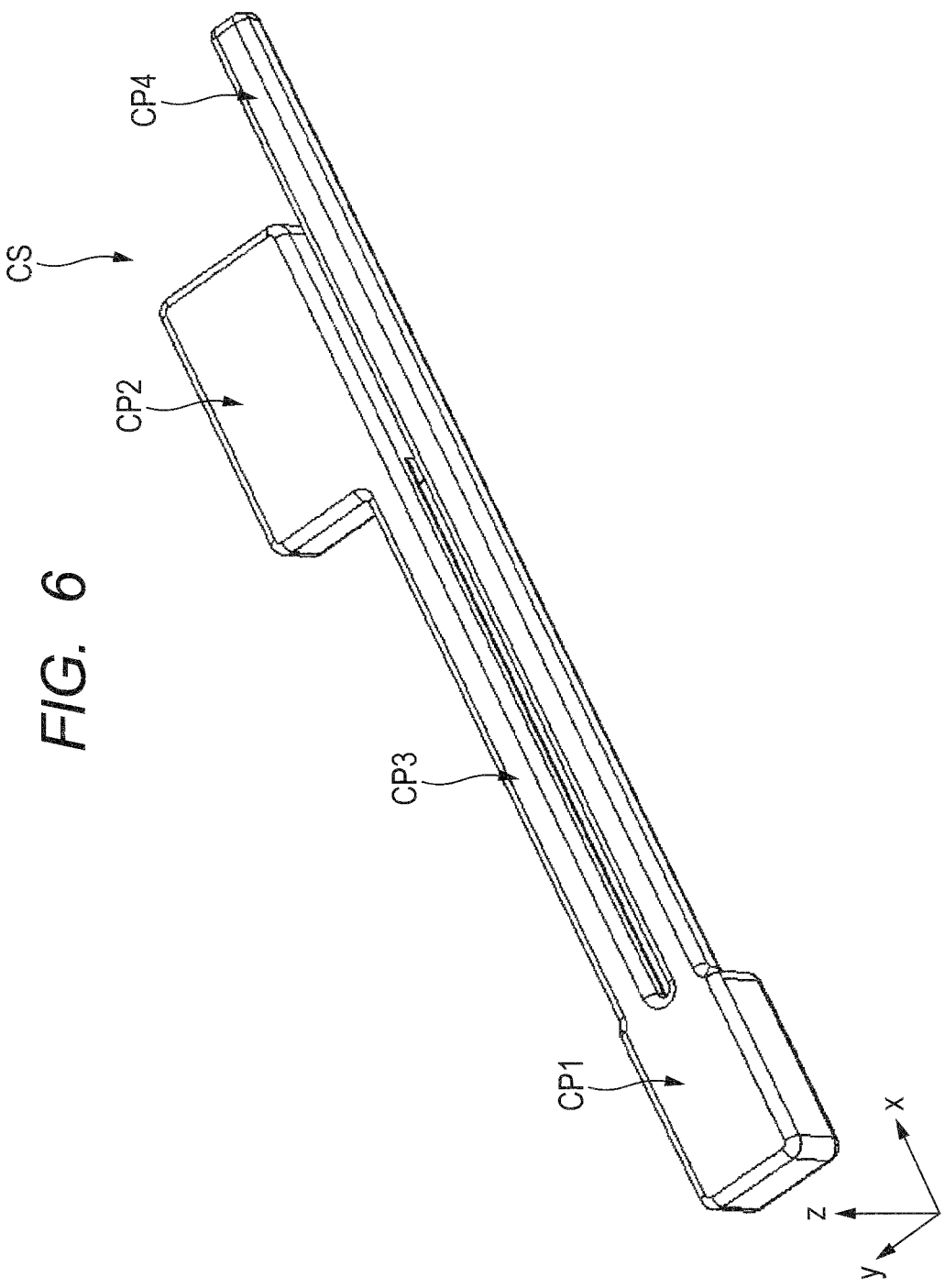

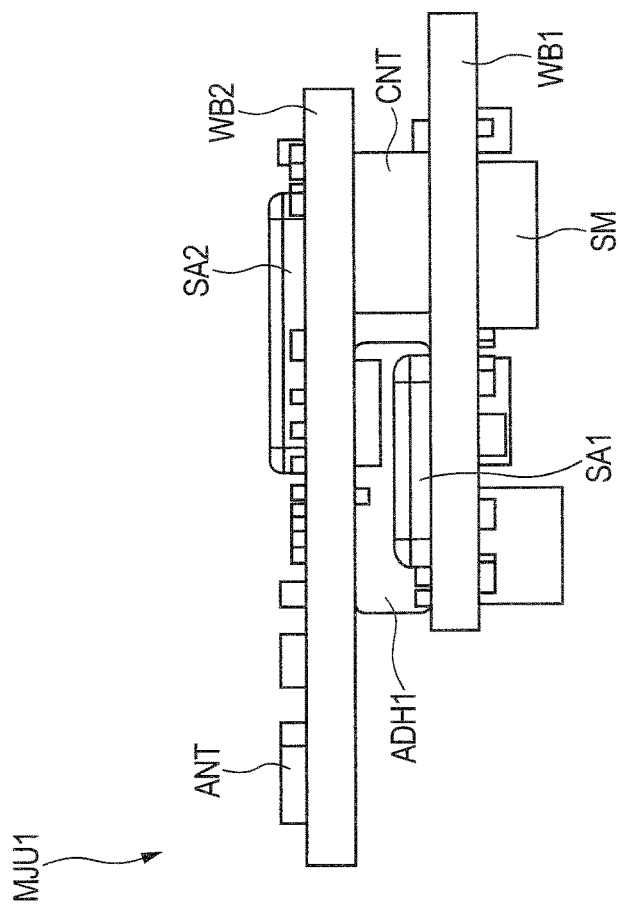
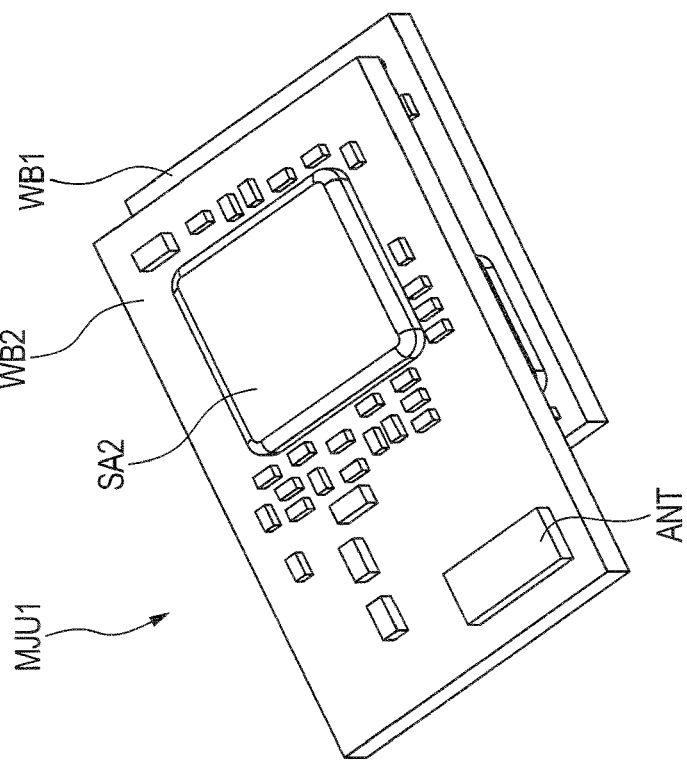

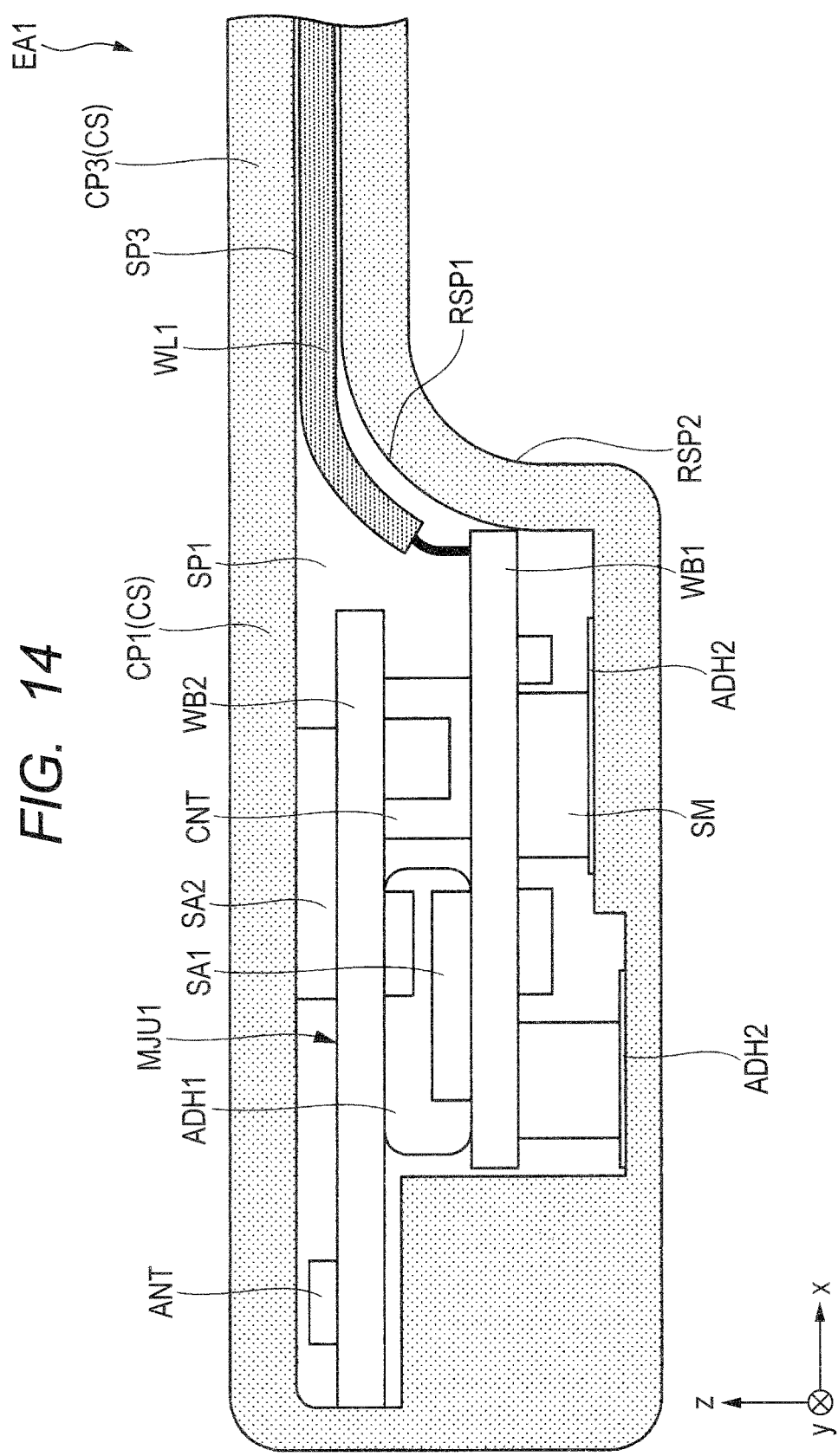

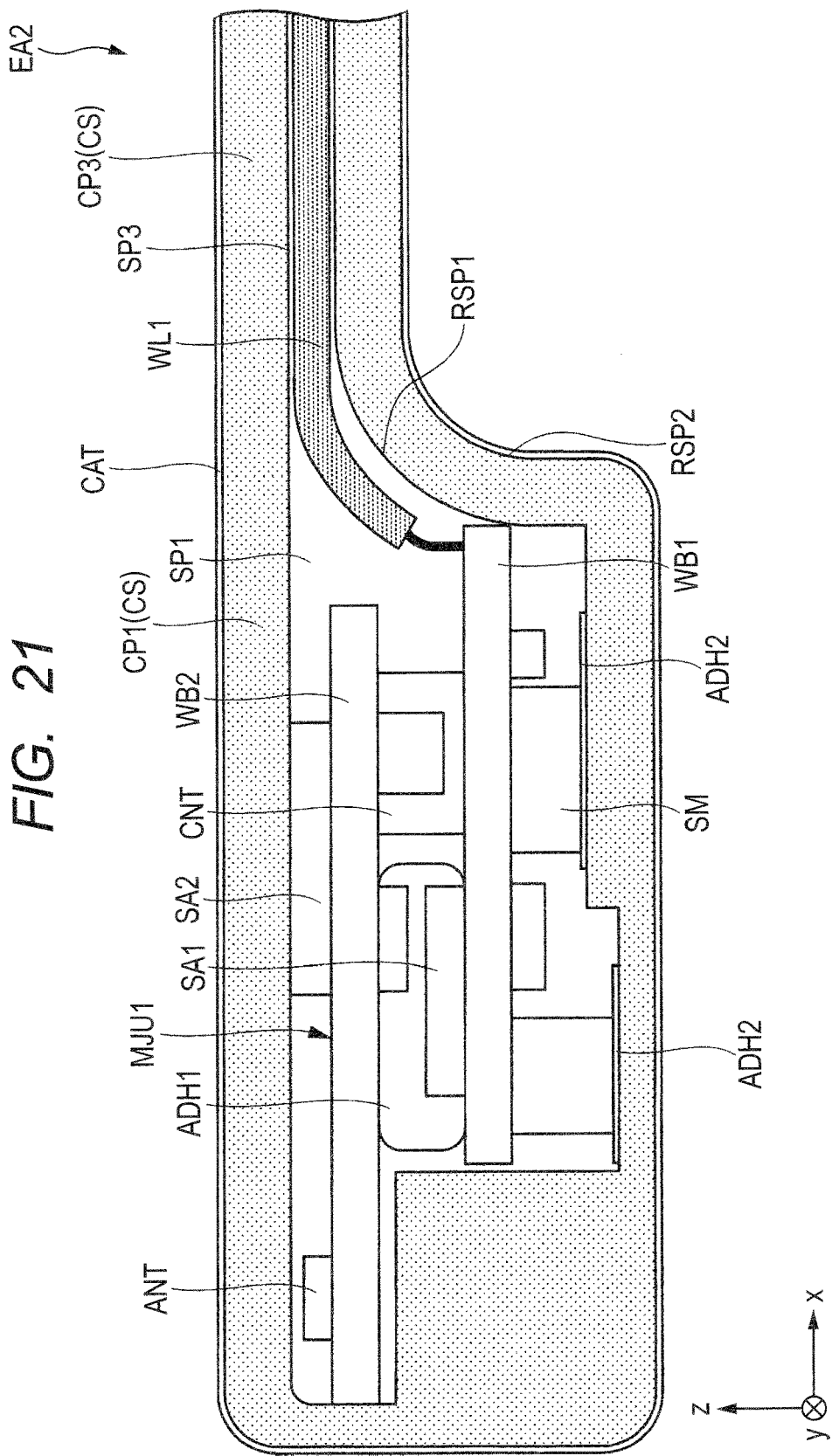

ELECTRONIC APPARATUS AND MANUFACTURING METHOD THEREFOR

CROSS-REFERENCE TO RELATED APPLICATIONS

The disclosure of Japanese Patent Application No. 2014-138888 filed on Jul. 4, 2014 including the specification, drawings and abstract is incorporated herein by reference in its entirety.

BACKGROUND

The present invention relates to an electronic apparatus and a manufacturing technology thereof, and to, for example, a technology effective when applied to an electronic apparatus which functions as a component of a wireless communication system, and a manufacturing technology thereof.

There has been described in Japanese Unexamined Patent Publication Laid-Open No. 2007-313594 (Patent Document 1), a structure in which a sensor control layer and an RF layer are respectively arranged in such a manner that the formation surfaces of a sensor control unit and an RF unit take the side being in contact with an MEMS layer, and sandwich the MEMS layer therebetween.

There has been described in Japanese Patent Application Publication No. 2006-505973 (Patent Document 2), a technology in which an antenna area is arranged over a substrate and an RF terminal is included in a die.

There has been described in International Patent Publication No. 2010/026990 (Patent Document 3), a technology in which a transmission circuit package and a reception circuit package are mounted over an antenna substrate as high-frequency circuit packages.

There has been described in Japanese Unexamined Patent Publication Laid-Open No. 2005-207797 (Patent Document 4), a technology having an RF interface block which converts a signal-processed sensing signal into a high frequency signal.

RELATED ART DOCUMENTS

Patent Documents

[Patent Document 1] Japanese Unexamined Patent Publication Laid-Open No. 2007-313594
[Patent Document 2] Japanese Patent Application Publication No. 2006-505973
[Patent Document 3] International Patent Publication No. 2010/026990
[Patent Document 4] Japanese Unexamined Patent Publication Laid-Open No. 2005-207797

SUMMARY

A wireless sensor network (may be called WSN) being a type of wireless communication system using a sensor has recently been attracting attention. In the wireless sensor network, data acquired at respective nodes are collected in a base station by wireless communication, and the collected data are analyzed to carry out tracking for an object, monitoring of the natural environment, etc.

For example, as the use form of the wireless sensor network, there has been examined that an electronic apparatus which configures a node is implanted in the body of an animal to acquire effective data about the behavior and state of the animal. In this case, it is important how the electronic apparatus configuring the node is implanted in the body of the animal without allowing the object animal to feel stress and its influence is prevented from being exerted on the behavior of the object animal, in terms of acquiring the effective data about the natural behavior and state of the object animal.

Other problems and novel features will be apparent from the description of the present specification and the accompanying drawings.

An electronic apparatus according to one aspect of the present invention includes a case having a first capacity part and a second capacity part separated from each other. A module unit having a sensor and a radio communication unit is accommodated in the first capacity part, and a battery is accommodated in the second capacity part.

Further, a method for manufacturing an electronic apparatus, according to one aspect of the present invention includes the steps of arranging a module unit in a first concave portion of a lower part, arranging a battery in a second concave portion of the lower part and arranging a wiring in a third concave portion of the lower part; and bonding the lower part and an upper part to each other to thereby seal the first concave portion, the second concave portion, and the third concave portion.

Furthermore, a method for manufacturing an electronic apparatus, according to one aspect of the present invention includes the steps of coupling a module unit and a battery by a wiring; arranging the module unit in a first concave portion of a first lower part and arranging a battery in a second concave portion of a second lower part; and bonding the first lower part and the first upper part to each other and arranging the second lower part and a second upper part to each other to thereby seal the first concave portion and the second concave portion.

According to the above one aspect, for example, even when an electronic apparatus which configures a node is implanted in the body of an animal, the object animal is hard to feel stress, and effective data about the natural behavior and state of the object animal can be acquired.

BRIEF DESCRIPTION OF THE DRAWINGS

FIG. 6 is a perspective diagram showing an external appearance configuration of a case in which components of an electronic apparatus according to an embodiment 1 are accommodated;

FIG. 11A is a perspective diagram showing a mounting structure of a module unit in the embodiment 1, and FIG. 11B is a side diagram showing the mounting structure of the module unit in the embodiment 1;

FIG. 14 is an enlarged diagram showing a part of FIG. 13 in an enlarged form;

FIG. 21 is a diagram showing a part of an electronic apparatus according to a modification 1 in an enlarged form;

DETAILED DESCRIPTION

Figure 1:
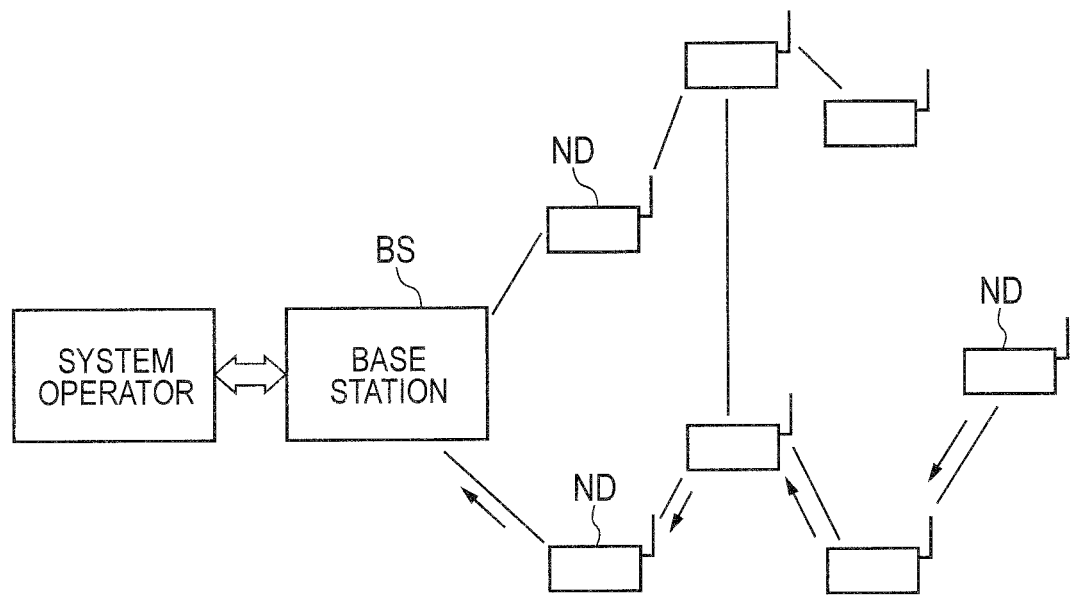
FIG. 1 is a typical diagram showing a general configuration example of an application using a wireless sensor network.

The invention will be described by being divided into a plurality of sections or embodiments whenever circumstances require it for convenience in the following embodiments. However, unless otherwise specified in particular, they are not irrelevant to one another. One thereof has to do with modifications, details and supplementary explanations of some or all of the other.

When reference is made to the number of elements or the like (including the number of pieces, numerical values, quantity, range, etc.) in the following embodiments, the number thereof is not limited to a specific number and may be greater than or less than or equal to the specific number unless otherwise specified in particular and definitely limited to the specific number in principle.

It is further needless to say that components (including element or factor steps, etc.) employed in the following embodiments are not always essential unless otherwise specified in particular and considered to be definitely essential in principle.

Similarly, when reference is made to the shapes, positional relations and the like of the components or the like in the following embodiments, they will include ones substantially analogous or similar to their shapes or the like except for where otherwise specified in particular and considered not to be definitely so in principle, etc. This is similarly applied even to the above-described numerical values and range.

The same reference numerals are respectively attached to the same members in principle in all the drawings for describing the embodiments, and a repeated description thereof will be omitted. Incidentally, even plan diagrams may be hatched for clarity of illustration.

Embodiment 1

<Wireless Sensor Network>

In the embodiment 1 to be described below, a wireless sensor network will be described by taking as an example of a wireless communication system. A technical idea in the embodiment 1 is not however limited to it, but is widely applicable to wireless communication systems each using a sensor.

The wireless sensor network taken as one example of the wireless communication system using the sensor is a technology which has been very attracting attention in recent years, and has been expected to be widely used. Nodes (terminals) which configure the wireless sensor network, are configured in such a manner as to obtain data outputted from sensors for temperature, illuminance, acceleration and the like, for example and transmit the so-obtained data by radio waves. For example, a "multi-hop ad hoc communication" to transfer the data obtained at the nodes by a bucket relay system between the nodes is used in the wireless sensor network.

That is, the related art mobile communication needs infrastructure development for base stations and a fixed network or the like for linking these. On the other hand, the wireless sensor network using the "multi-hop ad hock communication" is capable of communicating with autonomous routing of each node itself. Therefore, there is an advantage that the fixed network is unnecessary for the wireless sensor network, and the network can be constructed immediately by simply arranging nodes in an environment desired to construct the network. Incidentally, the form of the wireless sensor network is not limited to this, but includes a one-to-one basis, a star type and a mesh type. Any of them may be used.

Thus, the wireless sensor network can obtain an advantage that since the autonomous network can be configured by simply arranging the nodes, laying working at use site can be reduced. Further, since the dynamic state of the real world can be grasped by acquiring data outputted from each sensor, tracking for an object and monitoring of the natural environment are expected as applications promising for the wireless sensor network.

FIG. 1 is a typical diagram showing a general configuration example of an application using a wireless network sensor network. In FIG. 1, a plurality of nodes ND are arranged in the wireless sensor network. Each of the nodes ND is configured to observe a peripheral environment using a sensor function. Then, environment data observed at the nodes ND are collected in a base station BS by, for example, the "multi-hop ad hoc communication" between the nodes ND.

The base station BS is a computer accessible to the wireless sensor network and, for example, holds in an aggregated form, environment data obtained from the wireless sense network. Here, a computer for a system operator desired to acquire the environment data from the wireless sensor network accesses, for example, the base station BS to obtain required data and analyzes the so-obtained data, thereby making it possible to grasp the state of a real environment and execute processing requested by the application, based on the analyzed state.

<Configuration of Node>

Figure 2:
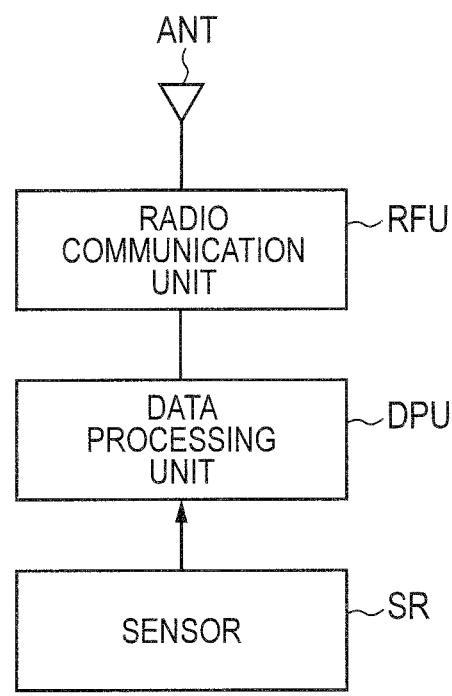
FIG. 2 is a block diagram showing a configuration of a node.

A description will subsequently be made about the nodes which configure the wireless sense network. FIG. 2 is a block diagram showing the configuration of each node. As shown in FIG. 2, each of the nodes configured as the components of the wireless sense network is equipped with, for example, a sensor SR, a data processing unit DPU, a radio communication unit RFU, and an antenna ANT.

The sensor SR is comprised of an element or device which detects physical quantities such as temperature, pressure, a flow rate, light, magnetism, etc. and the amounts of change in those. Further, the sensor SR is configured to convert the detected quantity to a suitable signal and output it therefrom. The sensor SR includes, for example, a temperature sensor, a pressure sensor, a flow rate sensor, an optical sensor, a magnetic sensor, an illuminance sensor, an acceleration sensor, an angular velocity sensor, or an image sensor or the like.

The data processing unit DPU is configured to process an output signal outputted from the sensor SR and output data of the processed signal. Also, the radio communication unit RFU is configured to convert the data processed by the data processing unit DPU to a signal of a radio frequency and transmit it from the antenna ANT. Further, the radio communication unit RFU is also configured to receive a radio frequency signal through the antenna ANT.

At the node configured in this way, a signal is outputted when a physical quantity is detected by the sensor SR. Then, the so-outputted signal is inputted to the data processing unit DPU. Further, the data processing unit DPU processes the inputted signal and outputs data of the processed signal to the radio communication unit RFU. Thereafter, the radio communication unit RFU converts the input data to a signal of a radio frequency and transmits the radio frequency signal from the antenna ANT. Thus, based on the physical quantity detected at the sensor SR, the signal of the radio frequency corresponding to the physical quantity is transmitted at the node.

<Detailed Configuration of Node>

Figure 3:
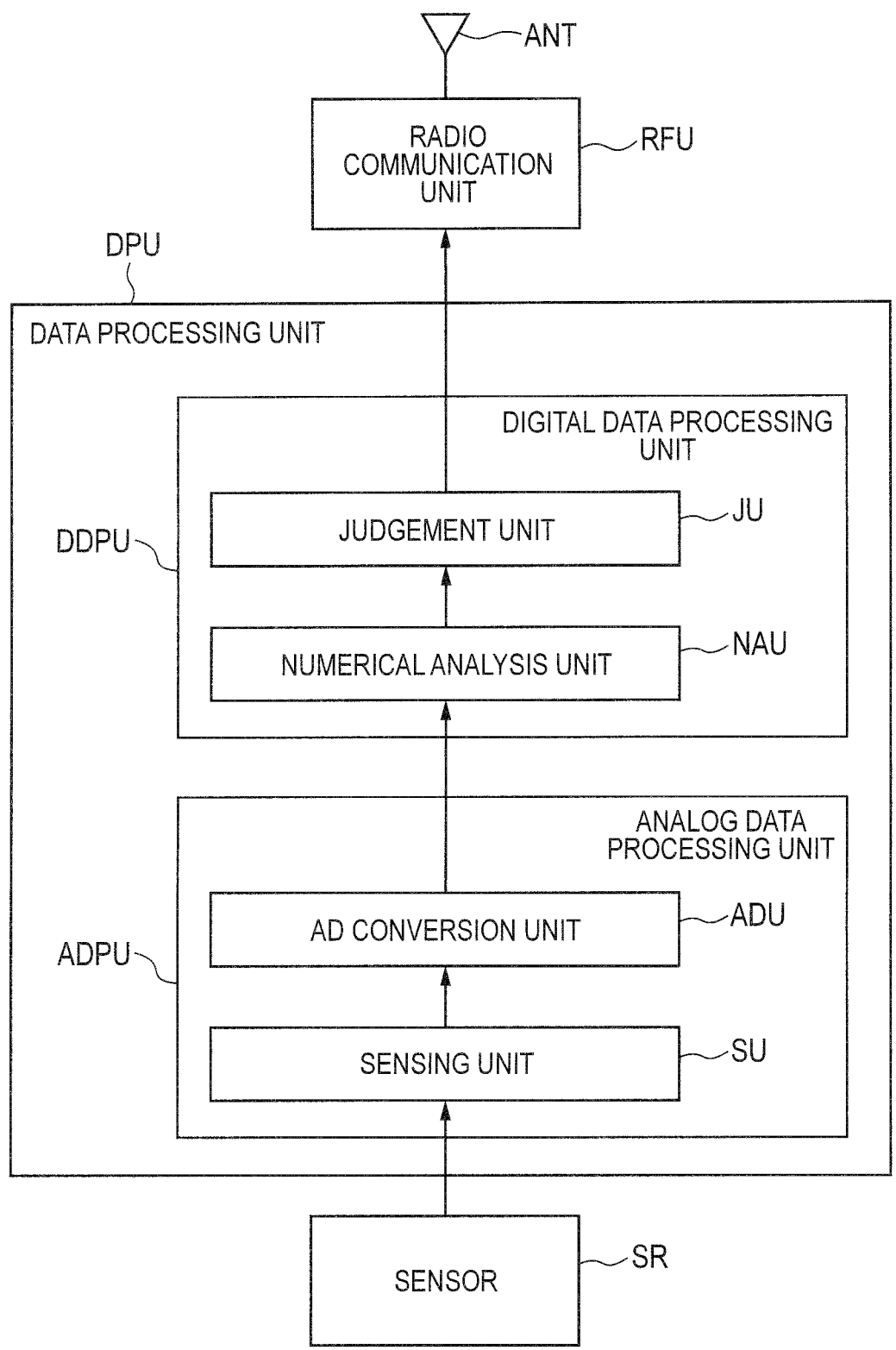
FIG. 3 is a block diagram principally showing a detailed configuration example of a data processing unit included in the node.

A description will further be made about one example of the detailed configuration of the node. FIG. 3 is a block diagram principally showing a detailed configuration example of the data processing unit DPU included in the node. As shown in FIG. 3, the data processing unit DPU included in the node is comprised of an analog data processing unit ADPU and a digital data processing unit DDPU. Then, the analog data processing unit ADPU is configured to include a sensing unit SU and an AD conversion unit ADU. The digital data processing unit DDPU is configured to include a numerical analysis unit NAU and a judgement unit JU.

Incidentally, there is also one which outputs a digital signal among the sensors SR. In this case, the analog data processing unit ADPU becomes unnecessary for the data processing unit DPU. The data processing unit DPU can also be comprised of the digital data processing unit DDPU. In this case, the analog data processing unit ADPU is built in the sensor SR. Although a description will however be made here about the form in which the data processing unit DPU is comprised of the analog data processing unit ADPU and the digital data processing unit DDPU as one example, the data processing unit DPU is not limited to this form.

A description will first be made about the analog data processing unit ADPU. The analog data processing unit ADPU is configured to input an analog signal outputted from the sensor SR therein and convert it into data easy to handle the analog signal. The analog data processing unit ADPU includes a sensing unit SU and an AD conversion unit ADU.

The sensing unit SU is configured to include, for example, an amplifier circuit, a transimpedance circuit, a filter circuit, etc. There is often a case where the output signal outputted from the sensor SR is small and the signal format thereof is not suitable for the processing of the digital data processing unit DDPU. Therefore, there is a need to provide a circuit which amplifies the small analog signal outputted from the sensor SR to an analog signal having a magnitude suitable for the input of the digital data processing unit DDPU. Further, there is also a case where the output signal outputted from the sensor SR is not a voltage, but a current. In this case, an AD conversion circuit which converts an analog signal to a digital signal can receive only a voltage signal. From this viewpoint, a circuit is required which amplifies a current signal to a voltage signal having an appropriate magnitude while converting the current signal to the voltage signal. This circuit is called the transimpedance circuit and is an analog circuit used for both the conversion circuit and the amplifier circuit. Further, an unnecessary frequency signal (noise) may be mixed in the output signal from the sensor signal SR. In this case, it becomes hard to acquire the output signal from the sensor SR due to the noise. Therefore, when, for example, the noise is a frequency higher than that of the output signal, there is a need to eliminate the nose by a low-pass filter circuit. On the other hand, when the noise is a frequency lower than that of the output signal, there is a need to eliminate the noise by a high-pass filter circuit.

Thus, since it is difficult to directly handle the output signal from the sensor SR, the analog data processing unit ADPU is provided. The analog data processing unit ADPU is provided with the sensing unit SU including the above-described amplifier circuit, transimpedance circuit and filter circuit. The series of analog circuits which configure the sensing unit SU are also called an "analog front end (AFE)".

Next, the AD conversion unit ADU is configured to convert analog data outputted from the sensing unit SU into digital data. That is, since the digital data processing unit DDPU can hand only the digital data, there is a need to convert the analog data to the digital data by the AD conversion unit ADU.

Subsequently, the digital data processing unit DDPU is configured to input the digital data outputted from the analog data processing unit ADPU therein and process the digital data. The digital data processing unit DDPU includes, for example, a numerical analysis unit NAU and a judgement unit JU. At this time, the digital data processing unit DDPU is comprised of, for example, a micon (MCU: Micro Control Unit).

The numerical analysis unit NAU is configured to input the digital data outputted from the analog data processing unit ADPU and perform numerical operation processing on the digital data, based on a program. Further, the judgement unit JU is configured to select, for example, data to be output to the radio communication unit RFU, based on the result of the numerical operation processing by the numerical analysis unit NAU.

The data processing unit DPU is configured in the above-described manner. The operation thereof will be described below. First, a physical quantity such as the temperature, pressure, flow rate, light, magnetism or the like is detected by the sensor SR. A weak detection signal taken as an analog signal is outputted from the sensor SR, based on the result of detection. Then, the output weak detection signal is inputted to the sensing unit SU in the analog data processing unit ADPU. Further, in the sensing unit SU, the input detection signal is amplified by the amplifier circuit. When the detection signal is not a voltage signal but a current signal, the current signal is converted to a voltage signal by the transimpedance circuit. Further, in order to remove noise included in the detection signal, the noise included in the detection signal is eliminated by the filter circuit. Thus, the sensing unit SU processes the detection signal (analog signal) inputted from the sensor SR to generate analog data (analog signal) and outputs it therefrom. Subsequently, the AD conversion unit ADU inputs the analog data outputted from the sensing unit SU therein and converts it to digital data. Thereafter, the digital data converted by the AD conversion unit ADU is inputted to the numerical analysis unit NAU in the digital data processing unit DDPU. Then, the numerical analysis unit NAU performs numerical operation processing, based on the input digital data. Thereafter, the judgment unit JU selects the digital data to be outputted to the radio communication unit RFU, based on the result of its numerical operation processing. Next, the digital data outputted from the digital data processing unit DDPU is inputted to the radio communication unit RFU where it is converted to a signal of a radio frequency, followed by being transmitted from the antenna ANT. Thus, at the node, the data based on the physical quantity detected by the sensor SR is generated and the signal of the radio frequency corresponding to the data is transmitted.

Figure 4:
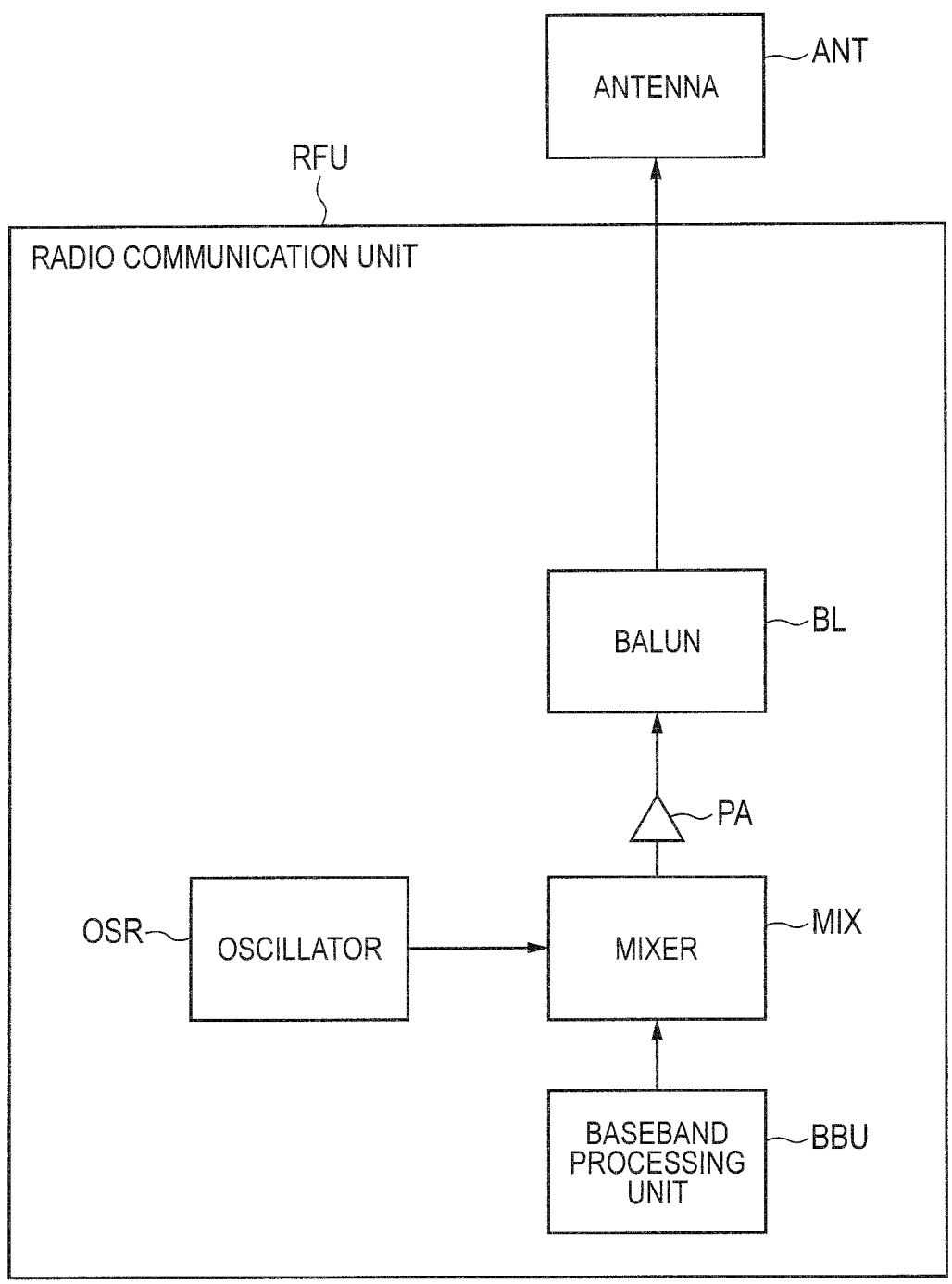
FIG. 4 is a block diagram principally showing a detailed configuration example of a transmission part of a radio communication unit included in the node.

A description will next be made about a detailed configuration example of the radio communication unit RFU included in the node. FIG. 4 is a block diagram principally showing a detailed configuration example of a transmission part of the radio communication unit RFU included in the node. In FIG. 4, the radio communication unit RFU has, for example, a baseband processing unit BBU, a mixer MIX, an oscillator OSR, a power amplifier PA, and a balun BL.

The baseband processing unit BBU is configured to generate a modulation baseband signal from the digital data inputted from the data processing unit and process the same. The oscillator OSR is configured to generate a carrier of a radio frequency. Also, the mixer MIX is configured to superimpose the baseband signal generated by the baseband processing unit BBU over the carrier generated at the oscillator OSR to generate a signal of a radio frequency. Further, the power amplifier PA is configured to amplify the signal of the radio frequency outputted from the mixer MIX. The balun BL is an element for converting electric signals held in balanced or unbalanced states.

The transmission part of the radio communication unit RFU is configured in the above-described manner. The operation thereof will be described below. First, the baseband processing unit BBU generates a modulation baseband signal from the digital data inputted from the data processing unit. Then, the baseband signal and the carrier generated at the oscillator OSR are mixed by the mixer MIX thereby to be modulated, whereby a signal of a radio frequency is generated. After the radio frequency signal has been amplified by the power amplifier PA, it is outputted from the radio communication unit RFU through the balun BL. Thereafter, the radio frequency signal outputted from the radio communication unit RFU is transmitted from the antenna ANT electrically coupled to the radio communication unit RFU. Thus, it is possible to transmit the radio frequency signal from the node.

Figure 5:
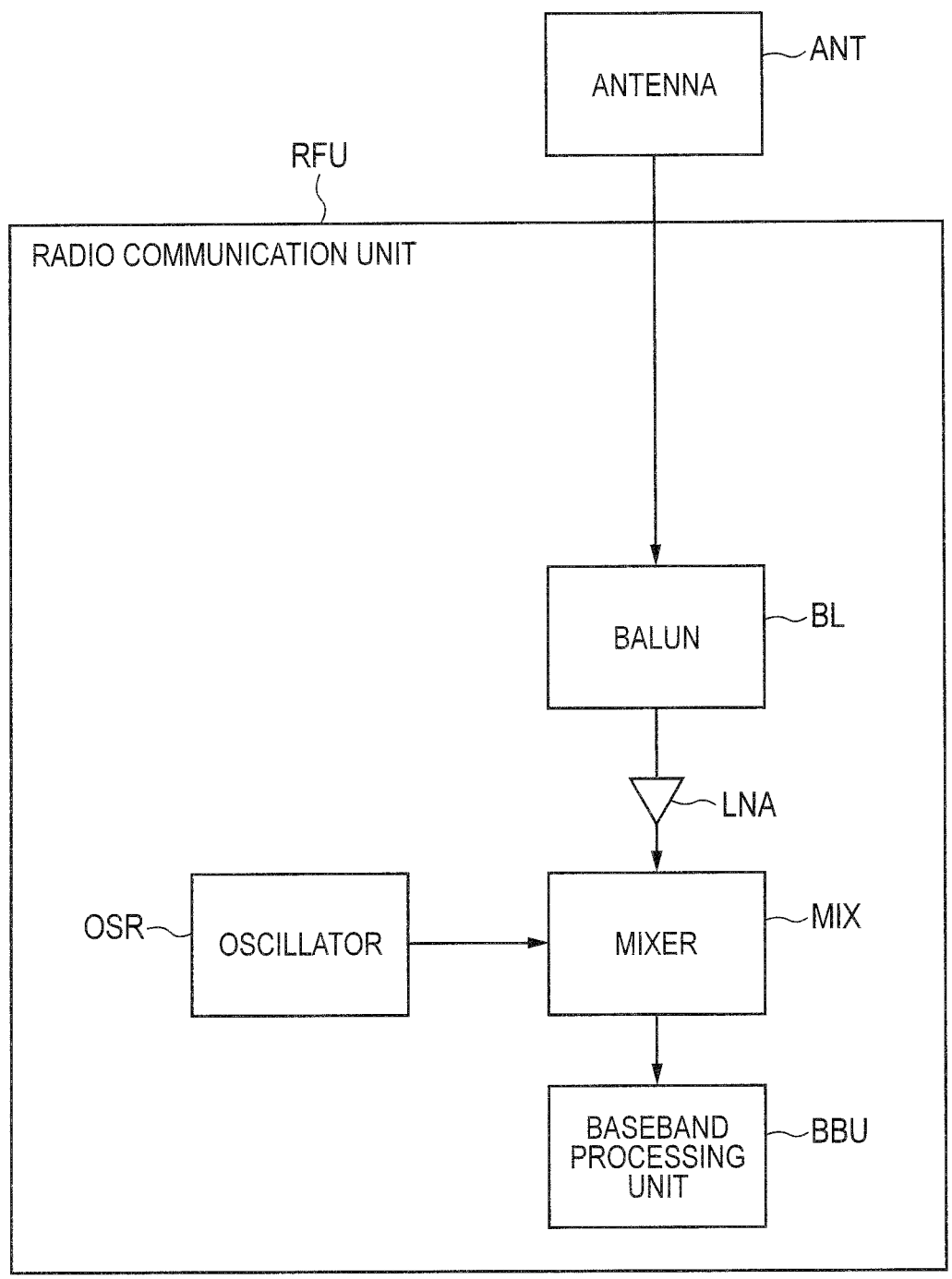
FIG. 5 is a block diagram principally showing a detailed configuration example of a reception part of the radio communication unit included in the node.

Subsequently, FIG. 5 is a block diagram principally showing a detailed configuration example of a reception part of the radio communication unit RFU included in the node. In FIG. 5, the radio communication unit RFU has a baseband processing unit BBU, a mixer MIX, an oscillator OSR, a low noise amplifier LNA, and a balun BL.

The balun BL is an element for converting electric signals held in balanced or unbalanced states. Further, the low noise amplifier LNA is configured to amplify a received weak reception signal. The oscillator OSR is configured to generate a carrier of a radio frequency. The mixer MIX is configured to superimpose the reception signal amplified by the low noise amplifier LNA over the carrier generated at the oscillator OSR to generate a baseband signal. The baseband processing unit BBU is configured to generate digital data from the demodulated baseband signal and process the same.

The reception part of the radio communication unit RFU is configured as described above. The operation thereof will be described below. First, the reception signal received by the antenna ANT is inputted to the low noise amplifier LNA through the balun BL, where it is amplified. Thereafter, the amplified reception signal is mixed with the carrier generated at the oscillator OSR by the mixer MIX thereby to be subject to demodulation to generate a baseband signal. Then, the demodulated baseband signal is converted to digital data and processed at the baseband processing unit BBU. It is possible to receive the reception signal at the node in the above-described manner.

<Basic Idea in the Embodiment 1>

As one use form of the above-described wireless sensor network, there has been examined that an electronic apparatus that configures a node is implanted in the body of each animal to collect effective data about the behaviors and states of the animals. In regard to this point, the present inventors are examining how node is desirably configured, in order to collect the effective data about the behaviors and states of the animals on the assumption that the nodes taken as the components of the wireless sensor network are implanted in the bodies of the animals.

For example, as the configuration of the node, there is considered a structure in which a module unit comprised of a sensor and a radio communication unit, and a battery for supplying power to the module unit are integrated with each other. Since, however, the node having the integrated structure includes the battery, the weight density of the entire node becomes large. As a result, when the node having the structure in which the module unit and the battery are integrated with each other is implanted in the body of each animal, the object animal becomes easy to feel stress. Thus, in this case, the behavior of the object animal is greatly affected by the implantation of the node into the body. It becomes difficult to obtain effective and significant data about the natural behavior and state of each object animal.

That is, the node having the structure in which the module unit and the battery are integrated with each other is considered to contribute to compactification of the entire node. When it is however considered that the node is implanted in the body of the animal, it cannot be said that the use of the node having the structure in which the module unit and the battery are integrated with each other is not appropriate in terms of acquiring the effective and significant data about the natural behavior and state of each object animal.

Therefore, in the present embodiment 1, the mounting structure of the electronic apparatus taken as the node is given a contrivance in terms of acquiring the effective and significant data about the natural behavior and state of the object animal on the assumption that the node is implanted in the body of the animal. The basic idea of this contrivance is an idea of achieving node load dispersion, which is completely opposite to the idea that the module unit and the battery are integrated with each other. According to this basic idea, since the local concentration of a load is mitigated at the node to be implanted, the object animal becomes hard to feel stress. As a result, according to the basic idea in the present embodiment 1 that decentralization of the load on the node is achieved, it is possible to acquire the effective and significant data about the natural behavior and state of the object animal.

Thus, the basic idea in the present embodiment 1 is of the idea of achieving the decentralization of the load on the node. A description will be made below about the mounting structure of the node in the present embodiment 1 in which the basic idea has been embodied. That is, the mounting structure of the electronic apparatus which makes it hard for the object animal to feel stress will be described on the assumption that the electronic apparatus configuring the node is implanted in the body of the animal.

<Configuration of Case in the Embodiment 1>

FIG. 6 is a perspective diagram showing an external appearance configuration of a case CS in which components of the electronic apparatus according to the present embodiment 1 are accommodated. Further, FIG. 7A is a top diagram showing the case CS in the present embodiment 1, and FIG. 7B is a side diagram showing the case CS in the present embodiment 1.

Figure 7A:
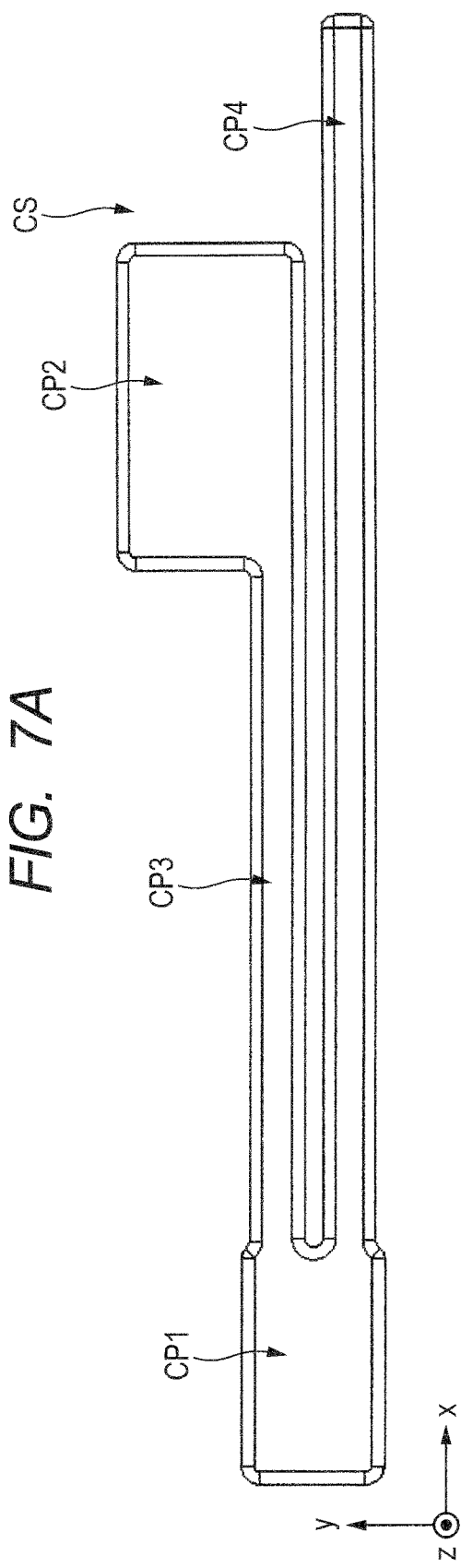
FIG. 7A is a top diagram showing the case in the embodiment 1.
Figure 7B:
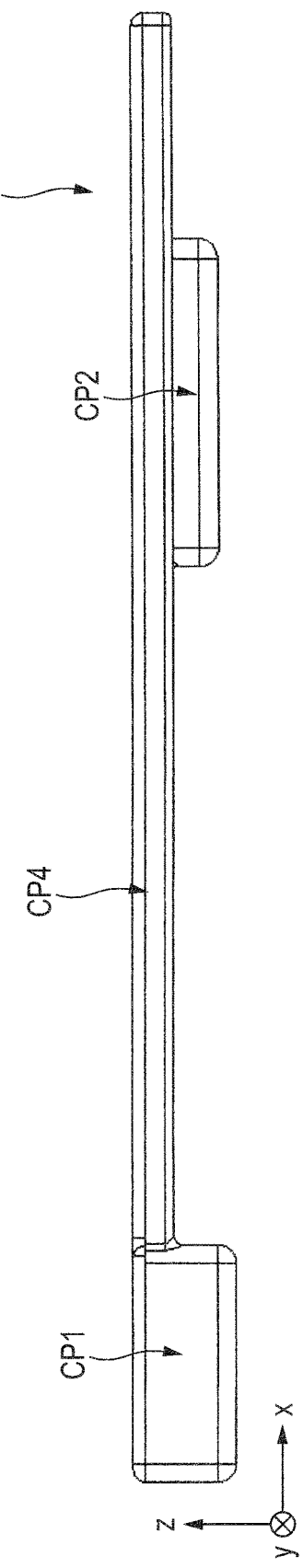
FIG. 7B is a side diagram showing the case in the embodiment 1.

As shown in FIG. 6 and FIGS. 7A and 7B, the case CS in the present embodiment 1 is equipped with a capacity part CP1 having a first space inside, a capacity part CP2 having a second space inside, a capacity part CP3 having a third space inside, and a capacity part CP4 having a fourth space inside. At this time, each of the capacity part CP1, the capacity part CP2, the capacity part CP3 and the capacity part CP4 is sealed. That is, the case CS is sealed.

Here, the capacity part CP1 and the capacity part CP2 are provided apart from each other. The capacity part CP1 and the capacity part CP2 are coupled by the capacity part CP3. Specifically, each of the capacity part CP1 and the capacity part CP2 has an approximately rectangular parallelepiped shape. The capacity part CP3 is formed from an approximately rectangular parallelepiped shape extending in an x direction so as to couple the capacity part CP1 and the capacity part CP2 arranged side by side in the x direction. Further, the capacity part CP4 is coupled to the capacity part CP1 and formed from an approximately rectangular parallelepiped shape which is in parallel to the capacity part CP3 and extends in the x direction.

The case CS in the present embodiment 1 is configured as described above. The components of the electronic apparatus are accommodated inside the case CS.

The case CS in the present embodiment 1 is formed of a biocompatible material. That is, each of the capacity part CP1, the capacity part CP2, the capacity part CP3, and the capacity part CP4 that configure the case CS is formed of the biocompatible material. As the biocompatible material, may be mentioned, for example, a biocompatible type silicone resin. The case CS formed of the biocompatible type silicone resin can be formed by, for example, compression molding or injection molding.

The hardness of the biocompatible type silicone resin can be adjusted in a range from about 25° to 75° according to the concentration of the additive or the like. However, in the case CS in the present embodiment 1, the hardness of the biocompatible type silicone resin is set to 50° in consideration of surface tackiness after its molding and stress applied to a post-implantation living body. However, the hardness of the biocompatible type silicone resin is not limited to it, but can be set as appropriate according to objects or applications for implantation.

<Mounting Structure of Components of Electronic Apparatus>

Figure 8:
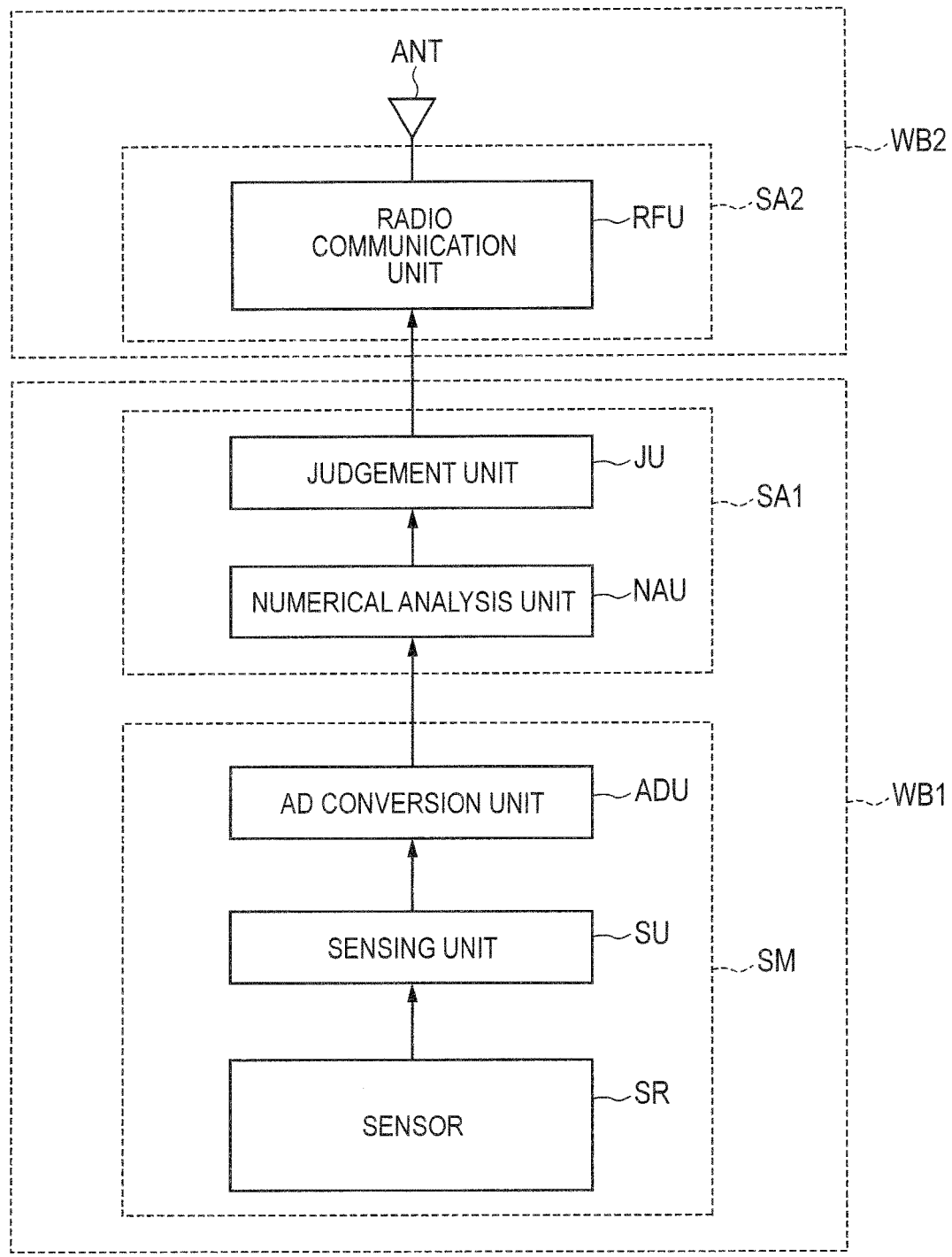
FIG. 8 is a diagram showing a corresponding relation between a functional configuration of the electronic apparatus (node) according to the embodiment 1 and mounting parts of the electronic apparatus.

A description will be made below about the mounting structure of the components of the electronic apparatus, which are accommodated inside the case CS. First, FIG. 8 is a diagram showing a corresponding relation between a functional configuration of the electronic apparatus (node) according to the present embodiment 1 and the mounting parts of the electronic apparatus. In FIG. 8, in the present embodiment 1, the sensor SR, sensing unit SU, and AD conversion unit ADU configure a sensor module SM in an integral fashion. On the other hand, the numerical analysis unit NAU and the judgement unit JU are formed in a semiconductor device SA1 which configures a MCU. Further, the sensor module SM and the semiconductor device SA1 are mounted over a common wiring board WB1.

On the other hand, the radio communication unit RFU and the antenna ANT are arranged in a wiring board WB2 used as a board different from the wiring board WB1. At this time, as shown in FIGS. 4 and 5, of the components of the radio communication unit RFU, the baseband processing unit BBU, oscillator OSR, mixer MIX, power amplifier PA, and low noise amplifier LNA are formed in a semiconductor device SA2 which configures a MCU.

Figure 9:
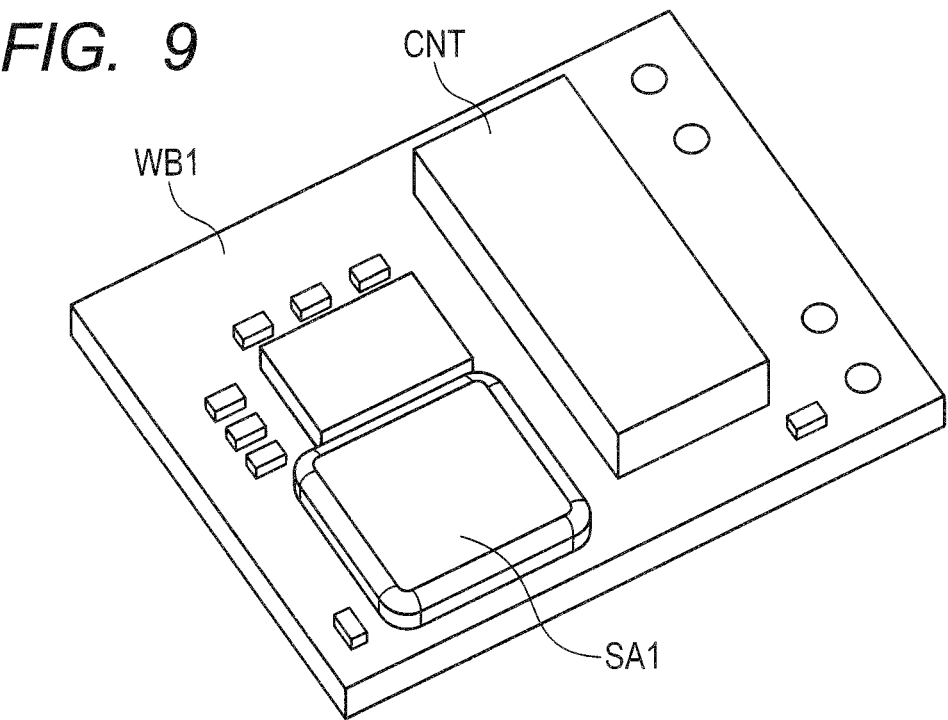
FIG. 9 is a perspective diagram typically showing a mounting structure of a wiring board mounted with electronic parts.

Subsequently, FIG. 9 is a perspective diagram typically showing a mounting structure of the wiring board WB1 mounted with electronic parts. As shown in FIG. 9, for example, the connector CNT and the semiconductor device SA1 are mounted over the surface (upper surface) of the wiring board WB1. The semiconductor device SA1 is formed with the MCU for realizing the numerical analysis unit NAU and the judgement unit JU shown in FIG. 8, etc. On the other hand, although not shown in FIG. 9, for example, the sensor module SM including the sensor SR, the sensing unit SU and the AD conversion unit ADU shown in FIG. 8 is arranged over the back surface (lower surface) of the wiring board WB1. That is, in the wiring board WB1 in the present embodiment 1, the electronic parts are mounted over both of the front and back surfaces.

Figure 10:
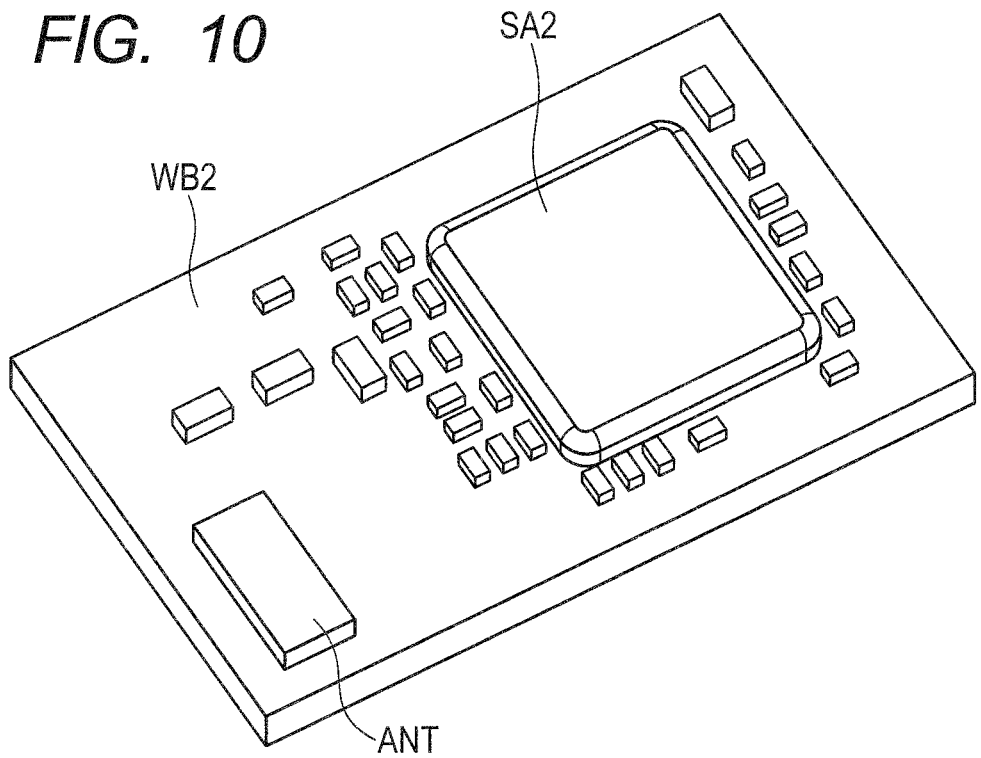
FIG. 10 is a perspective diagram typically showing a mounting structure of a wiring board mounted with electronic parts.

Next, FIG. 10 is a perspective diagram typically showing a mounting structure of the wiring board WB2 mounted with electronic parts. As shown in FIG. 10, the antenna (antenna unit) ANT comprised of, for example, a chip antenna, and the semiconductor device SA2 are mounted over the surface (upper surface) of the wiring board WB2. Here, the antenna ANT can also be comprised of a pattern antenna other than the chip antenna. The principal components of the radio communication unit RFU shown in FIG. 8 are formed in the semiconductor device SA2. As described above, the wiring board WB1 is mounted with at least the sensor (sensor module SM) which detects the physical quantity, whereas the wiring board WB2 is mounted with the radio communication unit RFU which transmits the data based on the output signal from the sensor. Accordingly, the module unit including the sensor module SM and the radio communication unit RFU has the wiring board WB1 shown in FIG. 9 and the wiring board WB2 shown in FIG. 10. The mounting structure of the module unit will be described below with reference to the drawings.

<Mounting Structure of Module Unit>

FIG. 11 is a diagram showing the mounting structure of the module unit MJU1 in the present embodiment 1. Specifically, FIG. 11A is a perspective diagram showing the mounting structure of the module unit MJU1 in the present embodiment 1, and FIG. 11B is a side diagram showing the mounting structure of the module unit MJU1 in the present embodiment 1.

First, as shown in FIG. 11A, the module unit MJU1 in the present embodiment 1 is comprised of a laminated structure of the wiring board WB1 shown in FIG. 9 and the wiring board WB2 shown in FIG. 10. For example, the module unit MJU1 in the present embodiment 1 is comprised of the wiring board WB1 arranged at the lower part of the wiring board WB2, and the wiring board WB2 arranged at the upper part of the wiring board WB1.

Described in detail, in the wiring board WB1 as shown in FIG. 11B, other electronic parts are mounted over the back surface of the wiring board WB1 together with the sensor module SM including the sensor. On the other hand, the electronic parts including the semiconductor device SA1 are mounted over the surface of the wiring board WB1 in addition to the connector CNT. In contrast, in the wiring board WB2, for example, a socket for inserting the socket CNT is formed in the back surface of the wiring board WB2. As a result, the wiring board WB1 and the wiring board WB2 can electrically and physically be coupled to each other by inserting the connector CNT formed in the surface of the wiring board WB1 arranged at the lower part into the socket formed in the back surface of the wiring board WB2 arranged at the upper part. Further, the wiring board WB1 and the wiring board WB2 are physically coupled even by an adhesive ADH1. The electronic apparatus including the antenna ANT and the semiconductor device SA2 is mounted over the surface of the wiring board WB2. The module unit MJU1 in the present embodiment 1 is formed in this manner.

In the module unit MJU1 in the present embodiment 1 configured in this way, the radio communication unit RFU and the sensor module SM included in the module unit MJU1 are separated from each other on the mounting structure. That is, in the present embodiment 1, the module unit MJU1 is comprised of the wiring board WB1 and the wiring board WB2 different from each other. The sensor module SM is realized by the electronic parts (mounting parts) mounted over the wiring board WB1. The radio communication unit RFU is realized by the electronic parts (mounting parts) mounted over the wiring board WB2.

A description will be made below about advantages obtained by configuring the radio communication unit RFU and the sensor module SM included in the module unit MJU1 so as to be separated on the mounting structure. For example, when the radio communication unit RFU and the sensor module SM are formed integrally with each other on the mounting structure to configure the module unit, it is necessary to acquire a wave authentication for each module unit different in sensor. The manufacturing cost of the module unit rises.

On the other hand, when the radio communication unit RFU and the sensor module SM are separated from each other on the mounting structure as in the module unit MJU1 in the present embodiment 1, only the sensor module SM can be customized by making in common the radio communication unit RFU at which the wave authentication is acquired. That is, since the wiring board WB2 formed with the radio communication unit RFU can be commonalized, there is no need to acquire the wave authentication for each module unit different in the type of sensor even when the configuration of the sensor module SM differs, thus making it possible to reduce the manufacturing cost of the entire module unit. The module unit MJU1 corresponding to the sensors different in type can be configured by making in common the mounting structure of the wiring board WB2 formed with the radio communication unit RFU and simply customizing only the mounting structure of the wiring board WB1 formed with the sensor module SM. Therefore, it is possible to improve the versatility of promoting the commonalization of the mounting parts that configure the module unit MJU1. Even from this viewpoint, the manufacturing cost of the module unit MJU1 can be reduced. That is, according to the separation configuration of the module unit MJU1 in the present embodiment 1, there can be obtained a remarkable advantageous effect that the manufacturing cost of the module unit MJU1 can greatly be reduced by the easiness of acquisition of the wave authentication by communalizing the radio communication unit RFU, and the improvement in the versatility due to the commonalization of the mounting parts.

Next, the module unit MJU1 in the present embodiment 1 is arranged in such a manner that the wiring board WB1 and the wiring board WB2 are laminated in their thickness direction. Thus, the planar size of the entire module unit MJU1 can be reduced. For example, when the radio communication unit RFU and the sensor module SM are arranged integrally over one wiring board, the number of mounting parts mounted over one wiring board is also increased, so that the planar size of the wiring board is made large, thus resulting in an increase in the planar size of the entire module unit.

On the other hand, when the wiring board WB2 arranged with the radio communication unit RFU and the antenna ANT is arranged in layers over the wiring board WB1 arranged with the sensor module SM as ins the module unit MJU1 in the present embodiment 1, the number of mounting parts mounted over the wiring board WB1 or the wiring board WB2 is also reduced. As a result, it is possible to reduce the planar sizes of the wiring board WB1 and the wiring board WB2. Further, the planar size of the entire module unit MJU1 can greatly be reduced by arranging the wiring board WB2 over the wiring board WB1 in the laminated form. As a result, according to the module unit MJU1 in the present embodiment 1, it is possible to attain miniaturization of the entire module unit MJU1 including the wiring board WB1 and the wiring board WB2.

Further, in the present embodiment 1, the wiring board WB1 and the wiring board WB2 are coupled to each other by the connector CNT. In this case, the wiring board WB1 and the wiring board WB2 are attachable/detachable. From this, for example, when a malfunction occurs in the radio communication unit RFU realized by the mounting parts mounted to the wiring board WB2 arranged in the upper layer, the wiring board WB2 having caused the malfunction can easily be detached from the wiring board WB1. Further, instead of the wiring board WB2 having caused the malfunction, a non-defective wiring board WB2 can be used as a non-defective module without any problem by being coupled to the wiring board WB1. Incidentally, in the present embodiment 1, in order to improve the coupling strength between the wiring board WB1 and the wiring board WB2, the wiring board WB1 and the wiring board WB2 are bonded not only by the connector CNT, but also by the adhesive ADH1. In this case, although easiness in attaching/detaching of the wiring board WB1 and the wiring board WB2 is considered to be sacrificed, the coupling strength between the wiring board WB1 and the wiring board WB2 can be improved without sacrificing the easiness in attaching/detaching of the wiring board WB1 and the wiring board WB2 by using as the adhesive ADH1, for example, an easily peelable material such as a silicon system adhesive material.

<Mounting Structure of Entire Electronic Apparatus Accommodated in Case>

Figure 12:
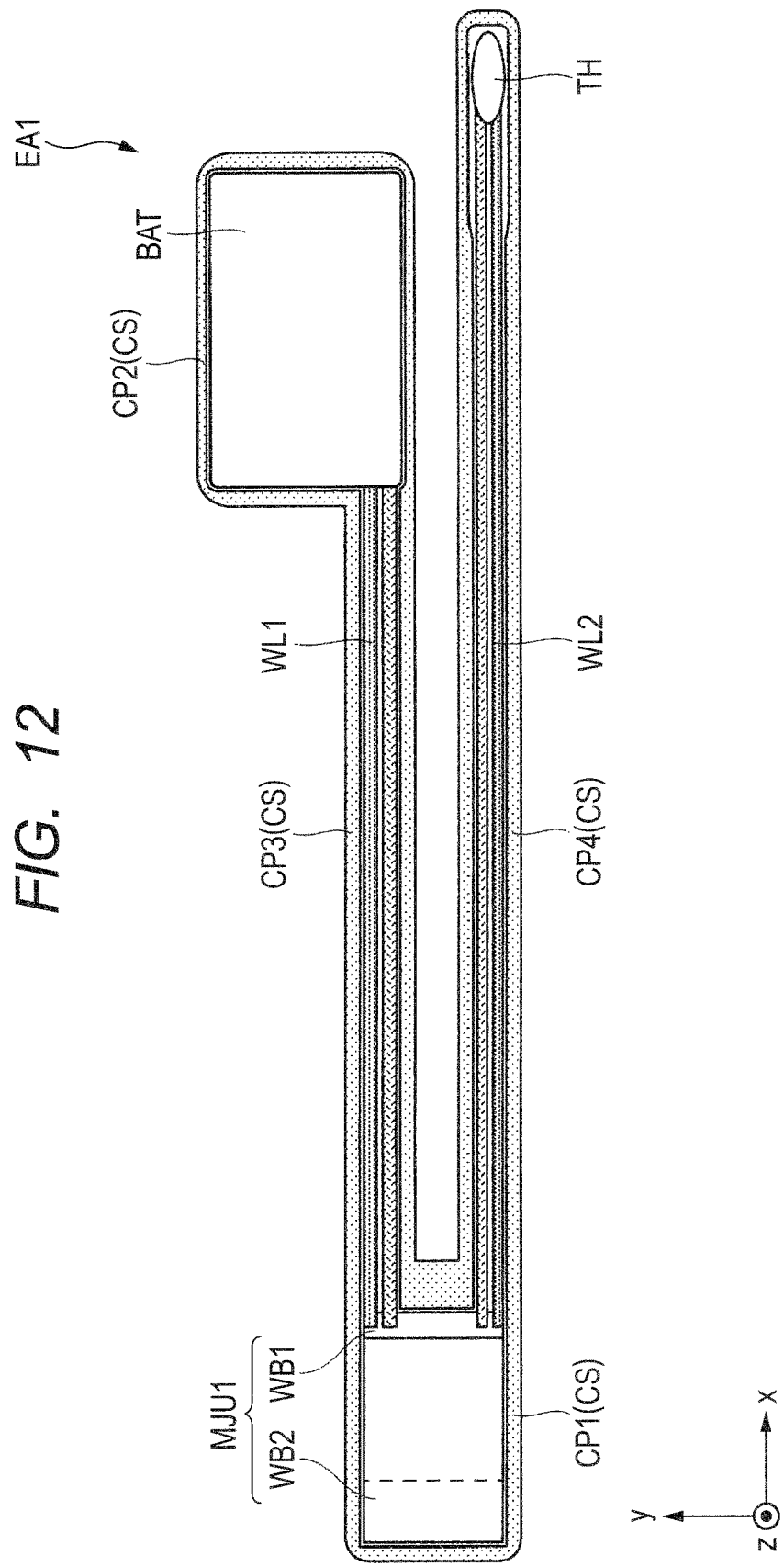
FIG. 12 is a typical transparent top diagram showing a mounting structure of the electronic apparatus according to the embodiment 1.
Figure 13:
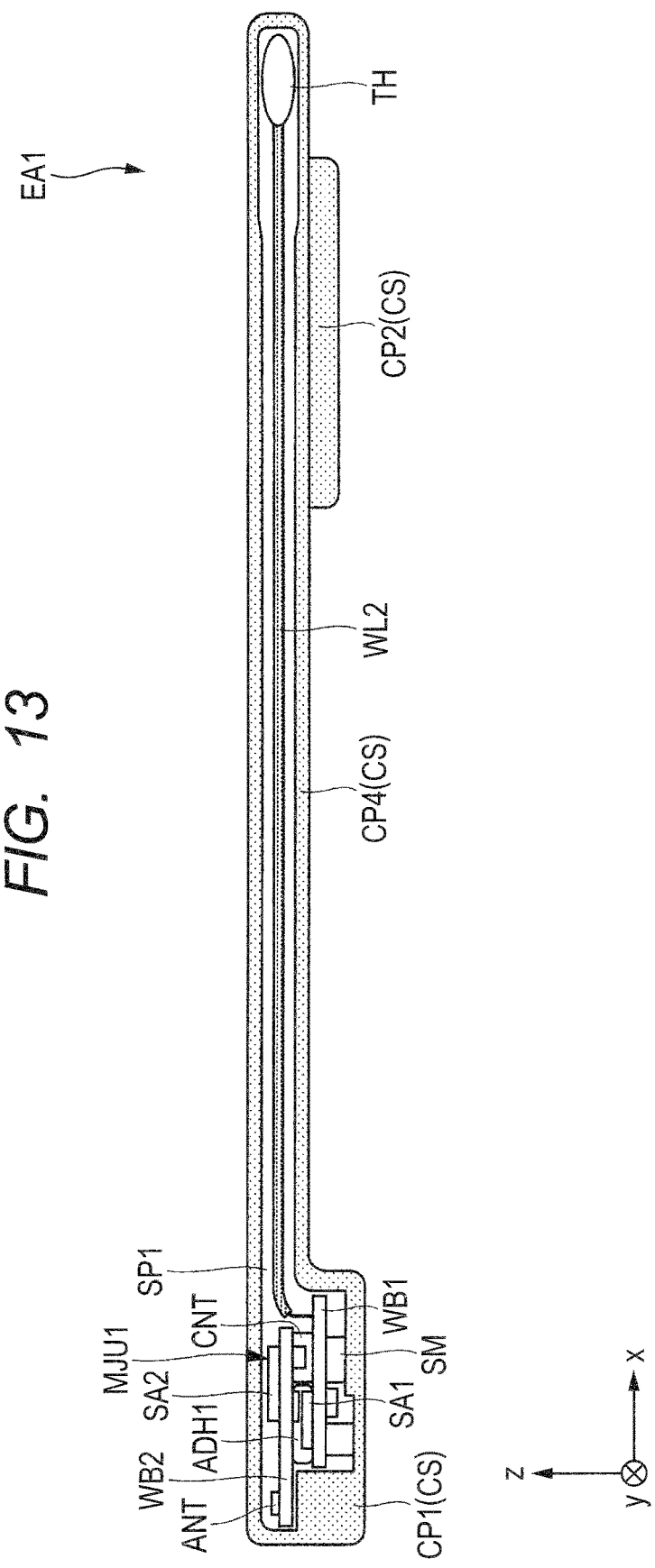
FIG. 13 is a typical transparent side diagram showing the mounting structure of the electronic apparatus according to the embodiment 1.

A description will subsequently be made about a mounting structure of the entire electronic apparatus EA1 accommodated in a case CS. FIG. 12 is a typical transparent top diagram showing the mounting structure of the electronic apparatus EA1 according to the present embodiment 1. Further, FIG. 13 is a typical transparent side diagram showing the mounting structure of the electronic apparatus EA1 according to the present embodiment 1. In FIGS. 12 and 13, a module unit MJU1 comprised of a laminated structure of a wiring board WB1 and a wiring board WB2 is accommodated in a first space lying inside a capacity part CP1 that configures part of the case CS. On the other hand, a battery BAT is accommodated in a second space lying inside a capacity part CP2 arranged away from the capacity part CP1. The battery BAT accommodated in the capacity part CP2 has the function of supplying power to the module unit MJU1 accommodated in the capacity part CP1, and can be comprised of, for example, a lithium ion battery.

In FIG. 12, a capacity part CP3 is arranged so as to be coupled to both of the capacity part CP1 having an approximately rectangular parallelepiped shape and the capacity part CP2 having an approximately rectangular parallelepiped shape, both of which are arranged away from each other. The capacity part CP3 has an approximately rectangular parallelepiped shape which extends in an x direction. A wiring WL1 is accommodated in a third space lying inside the capacity part CP3. The wiring WL1 is electrically coupled to the module unit MJU1 accommodated in the capacity part CP1 and electrically coupled to the battery BAT accommodated in the capacity part CP2. Thus, the wiring WL1 accommodated in the capacity part CP3 has a function as a coupling portion for electrically coupling the module unit MJU1 and the battery BAT.

Thus, it is possible to supply power from the battery BAT accommodated in the capacity part CP2 to the module unit MJU1 accommodated in the capacity part CP1 through the wiring WL1 accommodated in the capacity part CP3.

Further, as shown in FIGS. 12 and 13, a capacity part CP4 coupled to the capacity part CP1 and formed in an approximately rectangular parallelepiped shape extending in the x direction is provided in the case CS in the present embodiment 1. A temperature sensor is accommodated in a fourth space lying inside the capacity part CP4. The temperature sensor has, for example, the function of measuring a body temperature of a living body and is comprised of, for example, a thermistor TH and a wiring WL2. The wiring WL2 is electrically coupled to the module unit MJU1 accommodated in the capacity part CP1. Thus, the thermistor TH and the module unit MJU1 are electrically coupled to each other through the wiring WL2. That is, the wiring WL2 accommodated in the capacity part CP4 has the function of electrically coupling the module unit MJU1 and the thermistor TH.

Thus, a detection signal corresponding to the body temperature detected by the thermistor TH accommodated in the capacitor part CP4 is taken in the module unit MJU1 accommodated in the capacity part CP1 through the wiring WL2 accommodated in the capacity part CP4.

FIG. 14 is an enlarged diagram showing a part of FIG. 13 in an enlarged form. As shown in FIG. 14, a space SP1 is provided inside the capacity part CP1 which configures a part of the case CS. The module unit MJU1 shown in FIGS. 11A and 11B is accommodated in the space SP1. On the other hand, a space SP3 is provided inside the capacity part CP3 coupled to the capacity part CP1. The wiring WL1 is accommodated in the space SP3. Further, the wiring WL1 is electrically coupled by, for example, solder jointing, to the wiring board WB1 which is a partial component of the module unit MJU1.

Incidentally, although not shown in FIG. 14, the wiring WL1 is bonded even to the battery BAT by solder jointing. However, the wiring WL1 and the battery BAT can also be electrically coupled to each other by a connector. In this case, the battery BAT is attachable/detachable. For example, when the battery BAT is made up of a secondary battery capable of charging, it becomes easy to detach and charge the battery BAT.

Figure 15B:
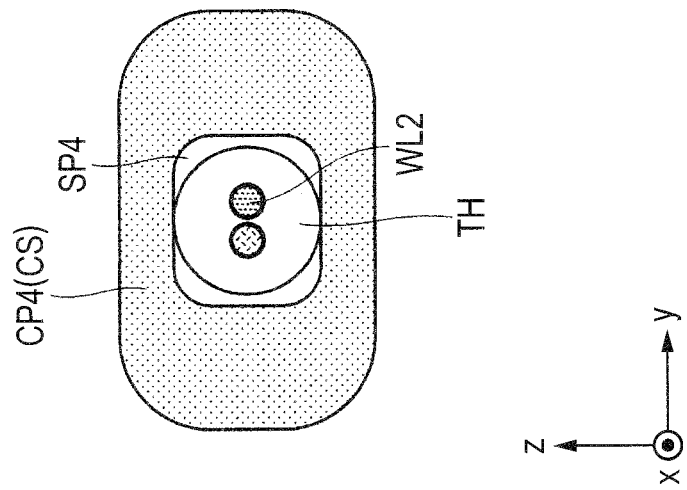
FIG. 15B is a typical sectional diagram of another capacity part which configures a part of the case.
Figure 15A:
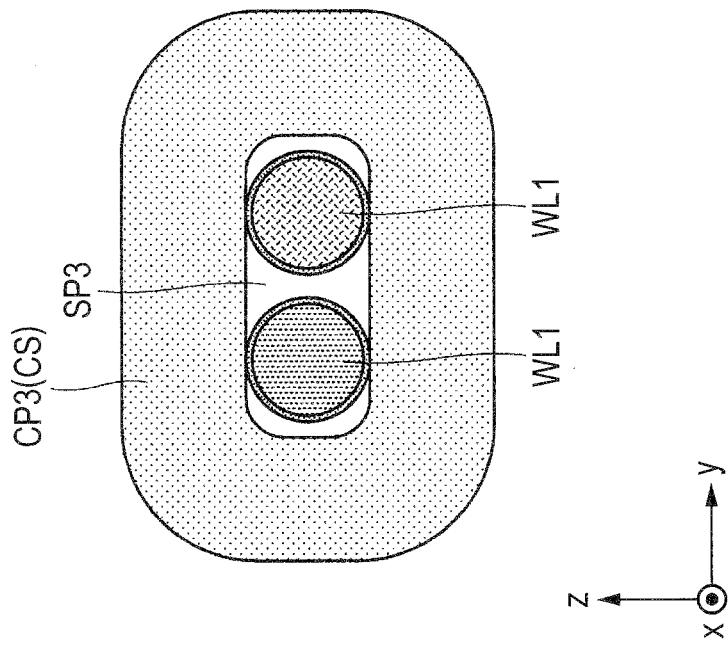
FIG. 15A is a typical sectional diagram of one capacity part which configures a part of the case.

FIG. 15A is a typical sectional diagram of the capacity part CP3 which configures a part of the case CS, and FIG. 15B is a typical sectional diagram of the capacity part CP4 which configures apart of the case CS. It is understood that as shown in FIG. 15A, a space SP3 is provided inside the capacity part CP3, and the wiring WL1 extending in the x direction is accommodated in the space SP3. It is understood from this viewpoint that the sectional shape of the space SP3 formed inside the capacity part CP3 needs to be at least larger than the sectional shape of the wiring WL1.

Further, as shown in FIG. 15B, a space SP4 is provided inside the capacity part CP4. The wiring WL2 extending in the x direction, and the thermistor TH coupled to the wiring WL2 are accommodated in the space SP4. At this time, it is understood that as shown in FIG. 15B, the sectional shape of the thermistor TH is larger than that of the wiring WL2. Thus, it is understood that the sectional shape of the space SP4 formed inside the capacity part CP4 needs to be at least larger than the sectional shape of the wiring WL2, and is further required to be larger than the sectional shape of the thermistor TH.

The electronic apparatus EA1 according to the present embodiment 1 configured as described above is an electronic apparatus which serves as the component (node) of the wireless communication system. The electronic apparatus EA1 includes the sealed case CS. At this time, the case CS has the capacity part CP1 having a hollow space thereinside, the capacity part CP2 provided away from the capacity part CP1 and having a hollow space thereinside, and a coupling portion for coupling the capacity part CP1 and the capacity part CP2. Then, the module unit MJU1 is accommodated in the hollow space of the capacity part CP1, and the battery BAT is accommodated in the hollow space of the capacity part CP2. Also, the coupling portion includes the wiring WL1 which electrically couples the module unit MJU1 and the battery BAT. Further, the module unit MJU1 has the sensor module SM including the sensor for detecting the physical quantity, and the radio communication unit RFU which transmits data based on an output signal from the sensor module SM.

Incidentally, a description will be made about specific outer dimensions of the electronic apparatus EA1 according to the present embodiment 1. The length in the x direction of the capacity part CP1 which configures the part of the case CS, is about 19 mm, the length in the y direction thereof is about 11 mm, and the thickness in the z direction thereof is about 7 mm. Also, the length in the x direction of the capacity part CP2 which configures the part of the case CS, is about 26 mm, the length in the y direction thereof is about 15 mm, and the thickness in the z direction thereof is about 6 mm. Further, the length in the x direction of the capacity part CP3 which configures the part of the case CS is about 54 mm, the length in the y direction thereof is about 4.4 mm, and the thickness in the z direction thereof is about 2 mm. Besides, the length in the x direction of the capacity part CP4 which configures the part of the case CS, is about 100 mm, the length in the y direction thereof is about 4.2 mm, and the thickness in the z direction thereof is about 2.2 mm.

Features in the Embodiment 1

The electronic apparatus EA1 according to the present embodiment 1 is configured as described above. A description will be made below about the features of the electronic apparatus EA1 according to the present embodiment 1.

A first feature point in the present embodiment 1 resides in that as shown in FIG. 12, for example, the module unit MJU1 and the battery BAT are arranged separated from each other. That is, the first feature point in the present embodiment 1 resides in that by adopting the case CS including the capacity part CP1 and the capacity part CP2 arranged separated from each other, the module unit MJU1 is accommodated in the space lying inside the capacity part CP1, and the battery BAT is accommodated in the space lying inside the capacity part CP2.

As a result, according to the present embodiment 1, the idea of achieving load decentralization of the electronic apparatus EA1, which is completely opposite to the idea that the module unit MJU1 and the battery BAT are integrated with each other, is embodied. That is, the load decentralization of the electronic apparatus EA1 is realized by the first feature point in the present embodiment 1 that the module unit MJU1 and the battery BAT are arranged separated from each other. That is, since the mass of the module unit MJU1 and the mass of the battery BAT occupy most of the mass of the entire electronic apparatus EA1, the load decentralization of the electronic apparatus EA1 can effectively be attained by arranging the module unit MJU1 and the battery BAT separated from each other.

Thus, when the electronic apparatus EA1 according to the present embodiment 1 is used for the node to be implanted, the local concentration of the load on the electronic apparatus EA1 is mitigated by the load decentralization between the module unit MJU1 and the battery BAT. Therefore, an object animal to implant the electronic apparatus EA1 becomes hard to feel stress. As a result, according to the first feature point in the present embodiment 1 in which the basic idea of achieving the load decentralization on the node has been embodied, it is possible to acquire effective and significant data about the natural behavior and state of an object animal.

Thus, according to the electronic apparatus EA1 in the present embodiment 1 in which the module unit MJU1 and the battery BAT are arranged separated from each other, for example, when it is desired to sense the vicinity of the back of the head of the object animal, the capacity part CP1 with the module unit MJU1 accommodated therein can be arranged in the neighborhood of the back of the head, and the capacity part CP2 with the battery BAT accommodated therein can be selectively arranged in relatively insensible parts such as the back, abdomen, etc. In this case, according to the first feature point in the present embodiment 1, the load that the object animal feels can be mitigated by the synergistic effect of the effect that the gravity center position of the entire electronic apparatus EA1 becomes low, and the effect that the loading of the load on the head of the object animal is mitigated. This means that the object animal to implant the electronic apparatus EA1 becomes hard to feel stress. Thus, it means that even if the electronic apparatus EA1 is implanted in the object animal, the natural behavior and state of the object animal can be maintained. As a result, according to the electronic apparatus EA1 in the present embodiment 1, it is possible to acquire effective and significant data about the natural behavior and state of the object animal even while implanting the electronic apparatus EA1 in the object animal.

Further, according to the first feature point in the present embodiment 1 that the module unit MJU1 and the battery BAT are arranged separated from each other, it is possible to attain not only load decentralization of the electronic apparatus EA1, but also volume dispersion of the electronic apparatus EA1.

For example, in the electronic apparatus in which the module unit MJU1 and the battery BAT are integrally arranged in layers, the volume concentration of the electronic apparatus occurs, so that the thickness of the electronic apparatus becomes thick. In this case, when the electronic apparatus is implanted in the object animal, the skin of the object animal is stretched because the thickness of the electronic apparatus is thick. This means that the object animal becomes easy to feel stress. Thus, there is a high possibility that the natural behavior and state of the object animal will be inhibited, and effective and significant data about the object animal cannot be acquired.

On the other hand, according to the first feature point in the present embodiment 1, since the module unit MJU1 and the battery BAT are arranged separated from each other, the thickness of the capacity part CP1 with the module unit MJU1 accommodated therein, and the thickness of the capacity part CP2 with the battery BAT accommodated therein can respectively be made thin. This means that even if the electronic apparatus EA1 according to the present embodiment 1 is implanted in the object animal, the skin of the object animal becomes hard to be stretched. Thus, according to the electronic apparatus EA1 of the present embodiment 1, the object animal is hard to feel stress. Hence, the natural behavior and state of the object animal are held, and effective and significant data about the object animal can be acquired.

Further, when attention is focused on the capacity part CP2 with the battery BAT accommodated therein, the choices of the battery capacity are also increased since the thickness of the capacity part CP2 can be made thin in the present embodiment 1. In other words, since the battery BAT having a relatively large battery capacity can be used while making it hard to give stress to the object animal, by the thinning of the capacity part CP2 according to the first feature point of the present embodiment 1, it is possible to prolong the lifetime of the electronic apparatus EA1 implanted in the object animal. This means that the effective and significant data about the object animal can be continuously acquired over a long period. As a result, there can be obtained an advantage that when the electronic apparatus EA1 according to the present embodiment 1 is used in each node of the wireless sensor network, a node can be provided which is long in maintenance cycle and is capable of reducing its running cost. In particular, in order to take out the electronic apparatus EA1 implanted in the object animal, there is a need to perform an operation on the object animal, and the maintenance of the node becomes easy to be complicated. Thus, the advantage that the maintenance period is long and the running cost can be reduced is particularly useful in an electronic apparatus assuming that it is implanted in the object animal as in the electronic apparatus EA1 according to the present embodiment 1.

As described above, according to the first feature point in the present embodiment 1 that the module unit MJU1 and the battery BAT are arranged separated from each other, the load decentralization of the electronic apparatus EA1 and the volume dispersion of the electronic apparatus EA1 are both realized. As a result, according to the electronic apparatus EA1 according to the present embodiment 1, the object animal is hard to feel stress by the synergistic effect of the load decentralization and the volume dispersion even if the electronic apparatus EA1 is implanted in the object animal. Thus, the natural behavior and state of the object animal are held. Therefore, there can be obtained a remarkable effect that the effective and significant data about the object animal can be obtained by adopting the electronic apparatus EA1 according to the present embodiment 1 in each node of the wireless sensor network.

Next, a second feature point in the present embodiment 1 resides in that as shown in FIG. 12, the capacity part CP1 with the module unit MJU1 accommodated therein, and the capacity part CP2 with the battery BAT accommodated therein are coupled by the capacity part CP3 long in the x direction corresponding to the separation direction of the capacity part CP1 from the capacity part CP2, and the wiring WL1 for electrically coupling the module unit MJU1 and the battery BAT is accommodated in the space lying inside the capacity part CP3. Thus, since the module unit MJU1 and the battery BAT arranged away from each other are electrically coupled by the wiring WL1, and the capacity part CP3 itself with the wiring WL1 accommodated therein has an approximately rectangular parallelepiped shape long in the x direction, the capacity part CP3 has flexibility. Thus, according to the second feature point in the present embodiment 1, when the electronic apparatus EA1 according to the present embodiment 1 is implanted in the object animal, the electronic apparatus EA1 is deformed following the movement of the object animal by the flexibility of the capacity part CP3 with the wiring WL1 accommodated therein. From this, even if the object animal moves, it becomes hard to feel stress by the deformation of the electronic apparatus EA1, and the natural behavior and state of the object animal can be suppressed from being inhibited. Therefore, there can be obtained a remarkable effect that effective and significant data about the object animal can be acquired by adopting the electronic apparatus EA1 according to the present embodiment 1 in each node of the wireless sensor network. That is, according to the electronic apparatus EA1 according to the present embodiment 1, as a result of the present embodiment having the second feature point that the flexibility of the capacity part CP3 with the wiring WL1 accommodated therein is provided, it is hard to cause a feeling of discomfort due to the electronic apparatus EA1 being implanted. Thus, the natural behavior and state of the object animal are secured.

From the above, according to the electronic apparatus EA1 according to the present embodiment 1, the flexibility of the capacity part CP3 is realized by configuring the capacity part CP3 in the form of a slender approximately rectangular shape together with the load decentralization of the electronic apparatus EA1 and the volume dispersion thereof realized by arranging the module unit MJU1 and the battery BAT so as to be separated from each other. As a result, the significant data corresponding to the natural behavior and state of the object animal can be acquired by the synergistic effect of the first and second feature points in the present embodiment 1.

Incidentally, in the electronic apparatus EA1 according to the present embodiment 1, as shown in FIG. 12, for example, the capacity part CP4 also has a slender approximately rectangular shape (approximately rectangular parallelepiped shape), and a material (e.g., a biocompatible type silicone resin) having flexibility is used as the material for the case CS, whereby the flexibility of the capacity part CP4 is implemented. That is, in the present embodiment 1, since the capacity part CP4 with the thermistor TH accommodated therein also has flexibility, the degree of freedom in arrangement of the thermistor TH can also be improved.

Subsequently, a third feature point in the present embodiment 1 resides in that as shown in FIG. 12, for example, the components of the electronic apparatus EA1 are accommodated inside the case CS comprised of the biocompatible material, and the case CS is sealed.

Thus, according to the third feature point in the present embodiment 1, first, the components of the electronic apparatus EA1 are accommodated inside the case CS comprised of biocompatible material. From this point, even if the electronic apparatus EA1 according to the present embodiment 1 is implanted in the body of the object animal, the in-body tissue of the object animal and the components of the electronic apparatus EA1 are not brought into direct contact with each other. The in-body tissue of the object animal directly contacts the case CS comprised of the biocompatible material having high compatibility with the in-body tissue.

Thus, the in-body tissue of the object animal becomes hard to be subject to the adverse effect or damage due to the components of the implanted electronic apparatus EA1. Even if the electronic apparatus EA1 is implanted, the health condition of the object animal is held. This means that in a broad sense, the natural behavior and state of the object animal are ensured. Thus, it is possible to acquire significant data corresponding to the natural behavior and state of the object animal.

Further, according to the third feature point in the present embodiment 1, the case CS comprised of the biocompatible material is sealed. From this, it is possible to prevent harmful substances from flowing out into the body of the object animal from the components of the electronic apparatus EA1 accommodated in the case CS. Even from this viewpoint, the in-body tissue of the object animal becomes hard to be subject to the adverse effect or damage due to the components of the implanted electronic apparatus EA1. Thus, the configuration in which the case CS comprised of the biocompatible material is sealed has a technical significance that the flowing out of the harmful substances into the body of the object animal from the electronic apparatus EA1 is prevented. If viewed from another angle, it can also be said that the configuration in which the case CS comprised of the biocompatible material is sealed has a technical significance that body fluids or the like produced in the in-body tissue of the object animal are prevented from entering the components of the electronic apparatus EA1 accommodated in the case CS.

That is, the third feature point in the present embodiment 1 has a technical significance that the adverse effect on the health of the object animal due to the electronic apparatus EA1 being implanted is suppressed, and a technical significance that the reliability of the electronic apparatus EA1 implanted in the body of the object animal is secured. Further, the direct technical significance of the third feature point in the present embodiment 1 resides in that the adverse effect on the health of the object animal is eliminated and the reliability of the implanted electronic apparatus EA1 is improved. However, through the direct technical significance, it can be said that the third feature point in the present embodiment 1 contributes to acquiring significant data corresponding to the natural behavior and state of the object animal.

Next, a fourth feature point in the present embodiment 1 resides in that a curved shape RSP is formed at a coupling part (lower part) of the capacity part CP1 and the capacity part CP3. It is thus possible to improve manufacturing easiness of the sealed case CS.

This point will be specifically described below. Although, for example, the sealed case CS is described in detail in an electronic apparatus manufacturing method to be described later, the case CS is comprised of a lower part and an upper part, and the lower part and the upper part are bonded to each other to manufacture the sealed case CS. Here, as shown in FIG. 14, the module unit MJU1 accommodated in the capacity part CP1, and the wiring WL1 accommodated in the capacity part CP3 are coupled by bonding by solder, the wiring WL1 to the wiring board WB1 taken as the component of the module unit MJU1. At this time, as shown in FIG. 14, the height (z direction) at which the wiring board WB1 is arranged, and the height (z direction) at which the wiring WL1 is arranged are different from each other. That is, a step occurs between the wiring board WB1 and the wiring WL1 as viewed in the x direction. In this case, when the coupling part (lower part) of the capacity part CP1 and the capacity part CP3 has a right-angled shape, the wiring WL1 is sealed into the case CS in such a manner as to be vertically bent in the vicinity of the coupling part. The wiring WL1 is however hard to be vertically bent. As a result, there is a fear that when the coupling part (lower part) of the capacity part CP1 and the capacity part CP3 is formed in the right-angled shape, the wiring WL1 is not completely bent at right angles in the vicinity of the coupling part, so that the wiring WL1 is not accommodated in the lower part and a part of the wiring WL1 protrudes from the lower part. In this case, the protruded part of the wiring WL1 inhibits the bonding between the lower part and the upper part, thus resulting in a high possibility that adhesion of the case CS will not be ensured. Further, when the wiring WL1 and the wiring WL2 are forcedly bent, the possibility of causing breakages in the wiring WL1 and the wiring WL2, and the possibility of due to application of stress to a solder junction part with the wiring board WB1, damaging the solder junction part are enhanced.

Therefore, in the present embodiment 1, as shown in FIG. 14, a curved shape RSP1 and a curved shape RSP2 are formed at the coupling part (lower part) of the capacity part CP1 and the capacity part CP3 (fourth feature point). In this case, even if the wiring WL1 is not completely bent at right angles in the vicinity of the coupling part, the flexibility (margin) at which the wiring WL1 is accommodated in the lower part is generated by the curved shape RSP1. As a result, according to the fourth feature point in the present embodiment 1, even when the step occurs between the wiring board WB1 and the wiring WL1, the wiring WL1 becomes easy to be accommodated in the lower part, and a part of the wiring WL1 can be suppressed from being protruded from the lower part. Thus, according to the fourth feature point in the present embodiment 1, the inhibition of bonding between the lower part and the upper part by the protruded part of wiring WL1 is hardly caused, whereby the adhesion of the case CS becomes easy to be ensured. That is, according to fourth feature point in the present embodiment 1, the degree of freedom in arranging the wiring WL1 is improved by the curved shape RSP1. As a result, it is possible to improve manufacturing easiness of the sealed case CS.

Thus, the fourth feature point of the present embodiment 1 that the curved shape RSP1 is formed at the coupling part (lower part) of the capacity part CP1 and the capacity part CP3 has a technical significance that even if the step occurs between the wiring board WB1 and the wiring WL1, the flexibility (margin) at which the wiring WL1 is accommodated in the lower part is generated. However, in the present embodiment 1, the point that the curved shape RSP2 is also formed is further included as the fourth feature point. The configuration to form the curved shape RSP2 also has a technical significance to be shown below. That is, the formation of the curved shape RSP2 at the coupling part (lower part) of the capacity part CP1 and the capacity part CP3 means that an improvement in the strength of the case CS can be attained and damaging to the in-body tissue of the object animal can be reduced when the electronic apparatus EA1 in the present embodiment 1 is implanted in the body of the object animal. From this point, the fourth feature point in the present embodiment 1 also has a technical significance that the curved shape RSP2 is formed to thereby enhance the strength of the case CS and reduce the damage to the in-body tissue of the object animal. It can be said that through this technical significance, the fourth feature point in the present embodiment 1 further contributes to acquiring significant data corresponding to the natural behavior and state of the object animal.

Incidentally, although a description has been made here about the configuration that the curved shape RSP1 and the curved shape RSP2 are formed at the coupling part (lower part) of the capacity part CP1 and the capacity part CP3, the configuration that a curve shape is formed at a coupling part (lower part) of the capacity part CP1 and the capacity part CP4 as shown in FIG. 13, for example is also effective. This is because the coupling configuration similar to the wiring WL1 which couples the wiring board WB1 and the battery BAT is taken even at the wiring WL2 which couples the wiring board WB1 and the thermistor TH. That is, it is considered that even where a step occurs between the wiring board WB1 and the wiring WL2 by the configuration that the curved shape is formed at the coupling part (lower part) of the capacity part CP1 and the capacity part CP4, the wiring WL2 becomes easy to be accommodated in the lower part, and a part of the wiring WL2 can be suppressed from protruding from the lower part.

Further, a curved shape may be formed even at the coupling part (refer to FIG. 12) of the capacity part CP3 with the wiring WL1 accommodated therein, and the capacity part CP2 with the battery BAT accommodated therein. In this case, for example, the step hardly occurs between the wiring WL1 and the coupling part of the wiring WL1 and the battery BAT. Therefore, the possibility of emerging problems that occur in the coupling part of the capacity part CP1 and the capacity part CP3 and the coupling part of the capacity part CP1 and the capacity part CP4 is low. It can however be said that since the technical significance that the damage to the in-body tissue of the object animal is reduced is exhibited, the curved shape is desirably formed even at the coupling part of the capacity part CP3 and the capacity part CP2.

Figure 16:
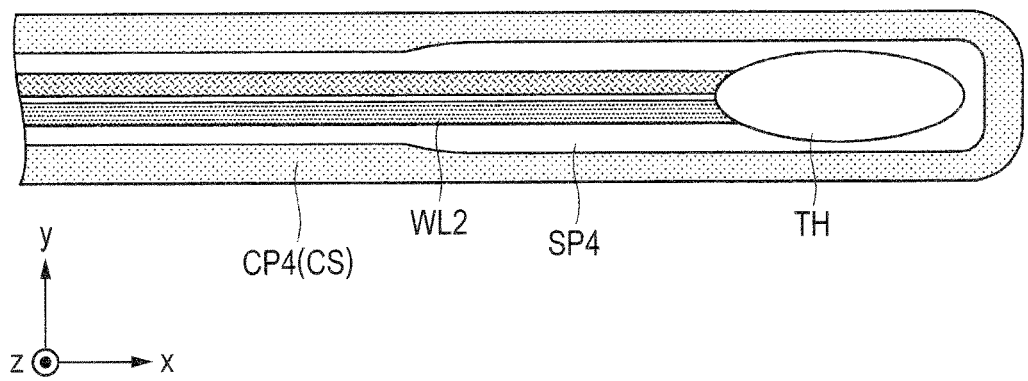
FIG. 16 is a typical transparent plan diagram showing a state in which a thermistor and a wiring are accommodated in an internal space of the capacitor part which configures a part of the case.

A description will subsequently be made about a fifth feature point in the present embodiment 1. FIG. 16 is a typical transparent plan diagram showing a state in which the thermistor TH and the wiring WL2 are accommodated in the internal space SP4 of the capacitor part CP4 which configures a part of the case CS. In FIG. 16, the fifth feature point in the present embodiment 1 resides in that the thickness of the capacity part CP4 with the thermistor TH accommodated therein is thinner than that of each of other parts of the capacity part CP4. Thus, it is possible to improve the accuracy of detection of the thermistor TH as the temperature sensor. That is, the thicker the thickness of the capacity part CP4 with the thermistor TH accommodated therein, the more the detection accuracy of the body temperature of the object animal at the thermistor TH is degraded. From this point, in the present embodiment 1, the thickness of the capacity part CP4 with the thermistor TH accommodated therein is made as thin as possible within a range in which the strength of the capacity part CP4 can be ensured. As a result, according to the present embodiment 1, the electronic apparatus EA1 implanted in the body of the object animal is capable of acquiring accurate data about the body temperature of the object animal.

For example, as shown in FIG. 15B, the thicknesses of the upper and lower parts of the capacity part CP4 with the thermistor TH accommodated therein can be made thinner than the thickness in the right to left direction of the capacity part CP4 within the range in which a bonding strength in the vertical direction can be maintained. Thus, according to the present embodiment 1, it is possible to suppress degradation in temperature detection sensitivity of the thermistor TH while maintaining the bonding strength of the capacity part CP4 with the thermistor TH accommodated therein.

Figure 17A:
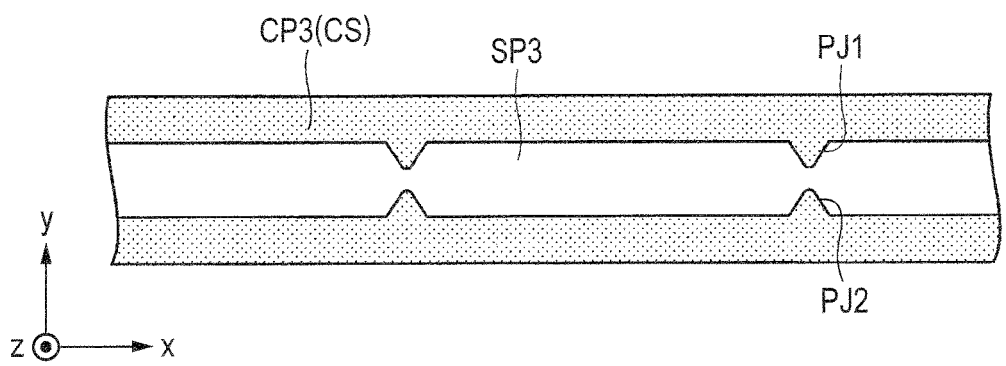
FIG. 17A is a transparent plan diagram of the capacity part configuring the part of the case as viewed from its top surface.
Figure 17B:
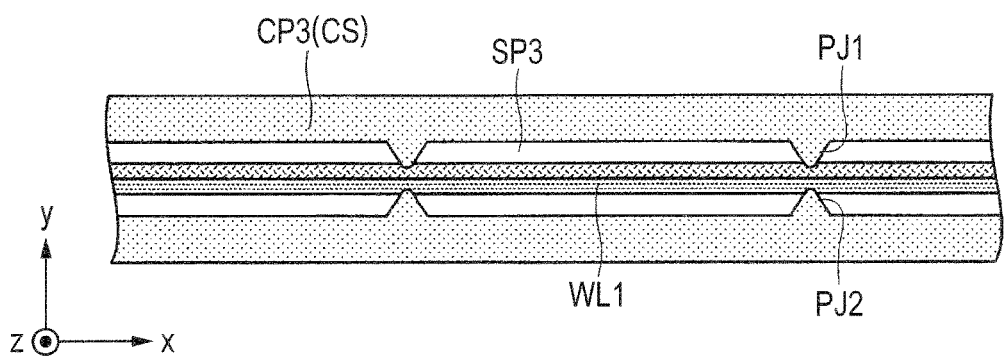
FIG. 17B is a transparent plan diagram showing a state in which a wiring is accommodated in the capacity part shown in FIG. 17A.

A sixth feature point in the present embodiment 1 will next be described. FIG. 17A is a transparent plan diagram of the capacity part CP3 configuring a part of the case CS as viewed from its top surface. In FIG. 17A, the sixth feature point in the present embodiment 1 resides in that a pair of projection parts PJ1 and PJ2 which projects toward the space SP3 lying inside the capacity part CP3 relative to each other is provided in the capacity part CP3. Thus, for example, as shown in FIG. 17B, when the wiring WL1 is accommodated in the space SP3 lying inside the capacity part CP3, the wiring WL1 can be sandwiched by the projection parts PJ1 and PJ2 which project relative to each other. In particular, a gap between the projection part PJ1 and the projection part PJ2 is designed to be equal to the diameter of the wiring WL1. In this case, when the wiring WL1 is inserted into the gap between the projection parts PJ1 and PJ2, the projection part PJ1 and the projection part PJ2 are distorted, so that the wiring WL1 is fixed by the projection part PJ1 and the projection part PJ2. Thus, the projection part PJ1 and the projection part PJ2 provided in the capacity part CP3 are provided to fix the position of the wiring WL1.

For example, the case CS is comprised of the upper and lower parts. The lower and upper parts are bonded to each other to manufacture the sealed case CS. Since, at this time, the space SP3 provided inside the capacity part CP3 is formed larger than the diameter of the wiring WL1, the position of the wiring WL1 is not fixed where the projection part PJ1 and the projection part PJ2 are not provided in the capacity part CP3. From this point, there is a fear that a part of the wiring WL1 protrudes from the lower part. In this case, the protruded part of the wiring WL1 inhibits bonding between the lower and upper parts, thus resulting in a possibility that adhesion of the case CS will not be ensured.

In this regard, in the present embodiment 1, the projection part PJ1 and the projection part PJ2 which protrude relative to each other, are provided in the capacity part CP3, and the wiring WL1 can be sandwiched by the projection part PJ1 and the projection part PJ2. As a result, according to the present embodiment 1, the position of the wiring WL1 can be fixed by the projection part PJ1 and the projection part PJ2. Thus, according to the present embodiment 1, since the wiring WL1 is securely fixed, the part of the wiring WL1 can be prevented from being protruded from the lower part. From the above, according to the present embodiment 1, the bonding between the lower part and the upper part can be reliably conducted and thus the adhesion of the case CS can be ensured. That is, according to the sixth feature point in the present embodiment 1, an improvement in the reliability of the electronic apparatus EA1 can be achieved through the fact that the adhesion of the case CS can be ensured.

Incidentally, when the electronic apparatus EA1 according to the present embodiment 1 is implanted in the body of the object animal or when the electronic apparatus EA1 is going to be deformed after its implantation, it is possible to suppress application of excessive stress onto the wiring WL1 by deformation of the projection part PJ1 and the projection PJ2 and a change in the position of the wiring WL1 relative to each of the projection part PJ1 and the projection part PJ2 from the suitable flexibility of the material that configures the capacity part CP3. Consequently, it is possible to prevent breakage of the wiring WL1 or the like, for example.

The sixth feature point in the present embodiment 1 is a technical idea that the position of the wiring WL1 is fixed by sandwiching the wiring WL1 by the projection part PJ1 and the projection part PJ2. This technical idea can be applied even to, for example, the wiring WL2 which couples the thermistor TH and the module unit MJU1.

Figure 18A:
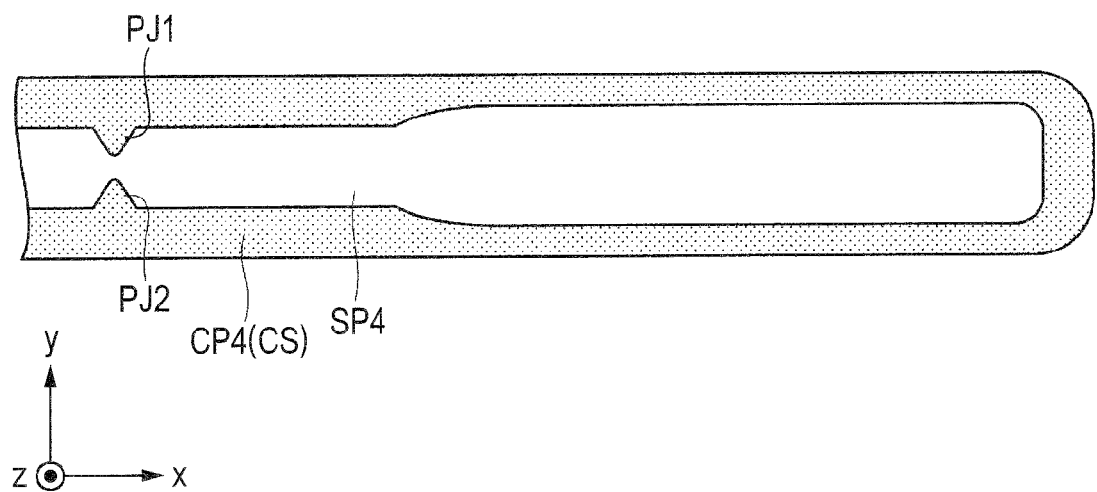
FIG. 18A is a transparent plan diagram of the capacity part configuring the part of the case as viewed from its top surface.
Figure 18B:
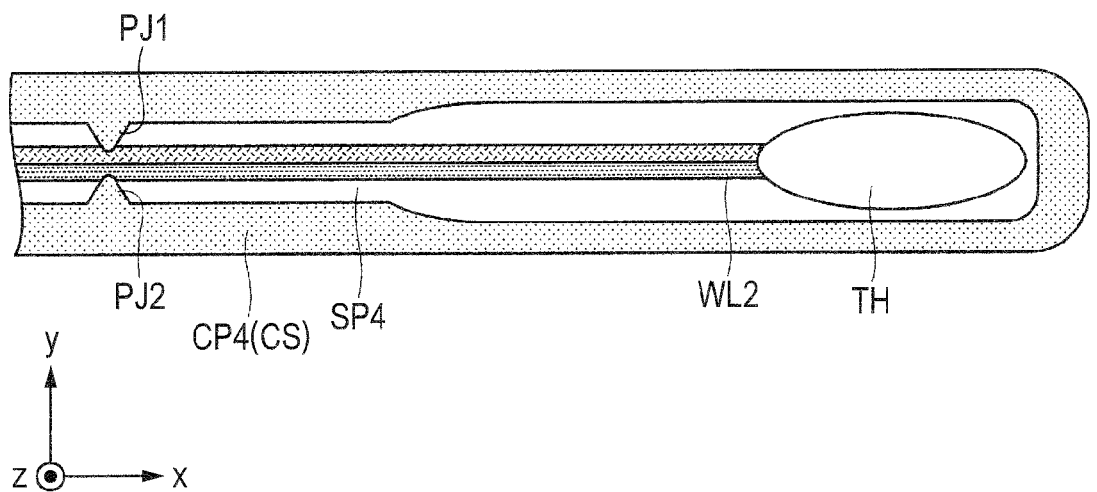
FIG. 18B is a transparent plan diagram showing a state in which the thermistor and the wiring are accommodated in the capacity part shown in FIG. 18A.

Specifically, FIG. 18A is a transparent plan diagram of the capacity part CP4 configuring a part of the case CS as viewed from its top surface. In FIG. 18A, a pair of projection parts PJ1 and PJ2 which projects toward the space SP4 lying inside the capacity part CP4 relative to each other is provided in the capacity part CP4. Thus, for example, as shown in FIG. 18B, when the wiring WL2 is accommodated in the space SP4 lying inside the capacity part CP4, the wiring WL2 can be sandwiched by the projection parts PJ1 and PJ2 which project relative to each other. As a result, according to the present embodiment 1, since the wiring WL2 is also securely fixed, a part of the wiring WL2 can be prevented from being protruded from the lower part. Thus, according to the present embodiment 1, the bonding between the lower part and the upper part can be securely carried out, thereby making it possible to ensure adhesion of the case CS.

Figure 19A:
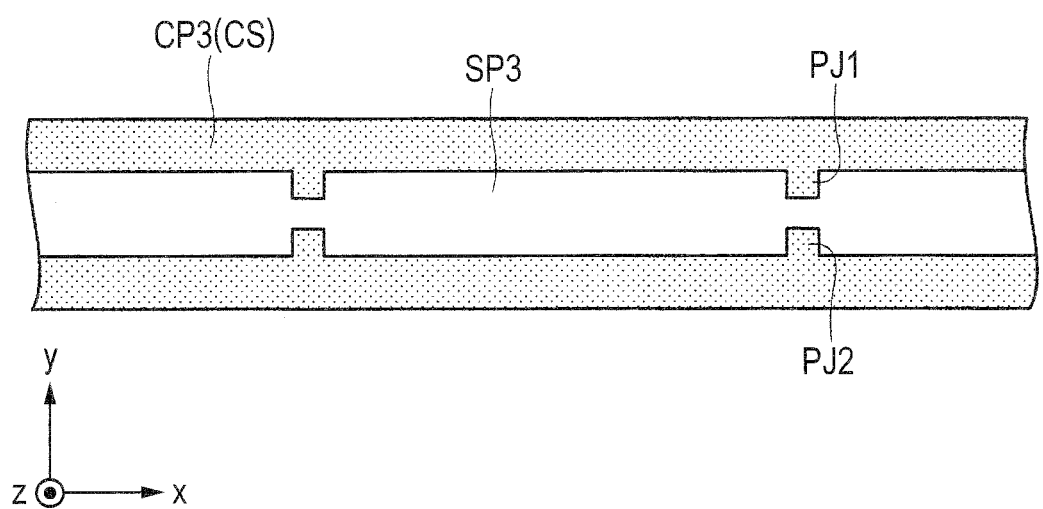
FIG. 19A is a transparent plan diagram of the capacity part configuring the part of the case as viewed from its top surface.
Figure 20A:
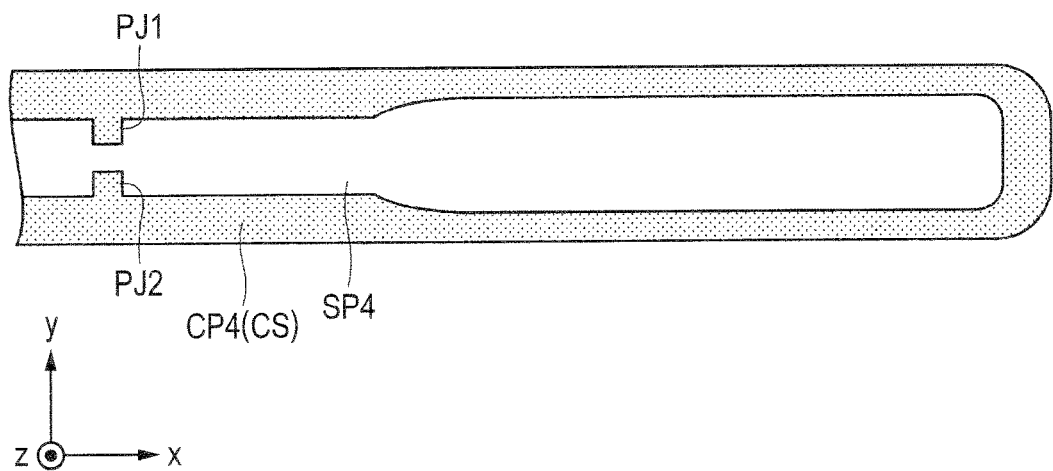
FIG. 20A is a transparent plan diagram of the capacity part configuring the part of the case as viewed from its top surface.

Incidentally, the shape of each of the projection parts PJ1 and PJ2 is not limited to the shapes shown in FIGS. 17A and 18A, but can also be set to, for example, shapes shown in FIGS. 19A and 20A. Further, the projection part (projection part PJ1 or projection part PJ2) may be configured to be provided only on the one sidewall of the capacity part CP3 or CP4.

Figure 19B:
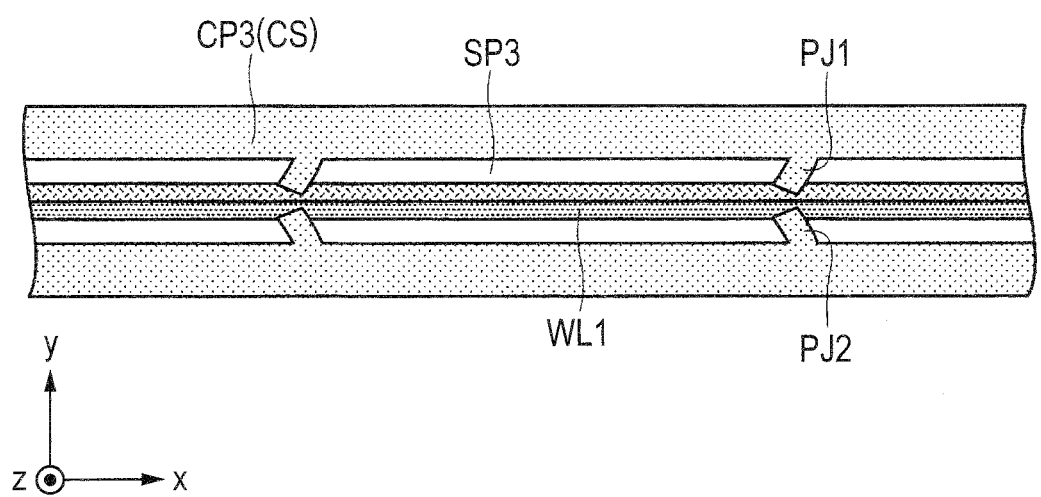
FIG. 19B is a transparent plan diagram showing a state in which the wiring is accommodated in the capacity part shown in FIG. 19A.

Specifically, FIG. 19A is a transparent plan diagram of the capacity part CP3 configuring a part of the case CS as viewed from its top surface, and FIG. 19B is a typical diagram showing the manner in which the wiring WL1 is sandwiched by a projection part PJ1 and a projection part PJ2 which are protruded relative to each other. In FIG. 19B, a gap between the projection part PJ1 and the projection part PJ2 is designed to be slightly smaller than the diameter of the wiring WL1. In this case, when the wiring WL1 is inserted into the gap between the projection part PJ1 and the projection part PJ2 as shown in FIG. 19B, the projection part PJ1 and the projection part PJ2 are flexed. Consequently, it is understood that the wiring WL1 is fixed by the projection part PJ1 and the projection part PJ2.

Figure 20B:
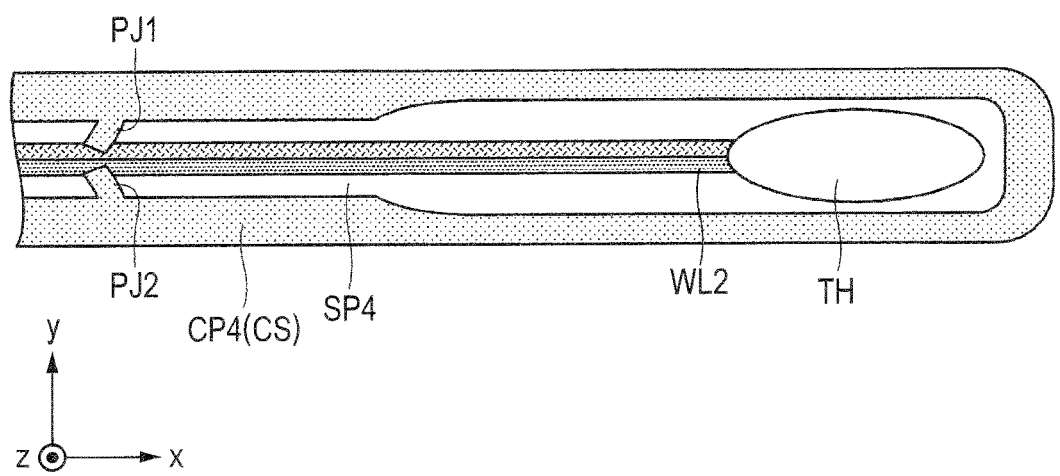
FIG. 20B is a transparent plan diagram showing a state in which the thermistor and the wiring are accommodated in the capacity part shown in FIG. 20A.

Similarly, FIG. 20A is a transparent plan diagram of the capacity part CP4 configuring a part of the case CS as viewed from its top surface, and FIG. 20B is a typical diagram showing the manner in which the wiring WL2 is sandwiched by a projection part PJ1 and a projection part PJ2 which are protruded relative to each other. When the wiring WL2 is inserted into a gap between the projection part PJ1 and the projection part PJ2 as shown in FIG. 20B, the projection part PJ1 and the projection part PJ2 are flexed. Consequently, it is understood that the wiring WL2 is fixed by the projection part PJ1 and the projection part PJ2.

Subsequently, a seventh feature point in the present embodiment 1 resides in that as shown in FIG. 14, the space SP1 is provided inside the capacity part CP1, and the module unit MJU1 is accommodated in the space SP1.

For example, the module unit MJU1 is also considered to be covered with a biocompatible material (sealing material) without providing the space SP1 inside the capacity part CP1. In this case, however, the module unit MJU1 becomes difficult to be taken out of the electronic apparatus EA1. This means that it becomes hard to reuse and repair the module unit MJU1 in the configuration in which the module unit MJU1 is covered with the biocompatible material (sealing material).

On the other hand, according to a seventh feature point in the present embodiment 1, the module unit MJU1 is accommodated in the space SP1 provided inside the capacity part CP1. In this case, there is obtained an advantage that it becomes easy to take out the module unit MJU1 from the electronic apparatus EA1, and it becomes easy to reuse and repair the module unit MJU1 and analyze its failure. Further, the electronic apparatus EA1 can be brought into less weight by providing the space SP1 inside the capacity part CP1.

In particular, the object animal in which the electronic apparatus EA1 is implanted becomes hard to feel stress with the weight reduction in the electronic apparatus EA1. From this point, it can be said that the seventh feature point in the present embodiment 1 that the module unit MJU1 is accommodated in the space SP1 provided inside the capacity part CP1 has not only an advantage that it becomes easy to reuse and repair the module unit MJU1 and analyze its failure, but also contributes to acquiring significant data corresponding to the natural behavior and state of the object animal through the weight reduction in the electronic apparatus EA1.

However, according to the seventh feature point in the present embodiment 1, there also exists a demerit in that the module unit MJU1 becomes easy to rattle. In this regard, in the present embodiment 1, as shown in FIG. 14, a contrivance for providing depressions and projections is applied to the shape of the capacity part CP1 to fit to a concave-convex shape of the module unit MJU1. That is, in the present embodiment 1, a contrivance for providing the depressions and projections in the inner wall shape of the capacity part CP1 is applied to reflect a concave-convex shape with part mounting of the module unit MJU1. Thus, according to the electronic apparatus EA1 according to the present embodiment 1, it is possible to reduce the rattling of the module unit MJU1.

Incidentally, what extent the inner wall shape of the capacity part CP1 configuring the part of the case CS is to be reflected on the concave-convex shape of the module unit MJU1 needs to consider even economy upon design of the case CS because it influences even the price and durability of a mold for manufacturing the case CS.

In the present embodiment 1, a further contrivance is applied in terms of reducing the rattling of the module unit MJU1. This point of contrivance corresponds to an eighth feature point in the present embodiment 1.

The eighth feature point in the present embodiment 1 will be described below. As shown in FIG. 14, the eighth feature point in the present embodiment 1 resides in that the module unit MJU1 accommodated in the space SP1 existing inside the capacity part CP1, and the bottom face of the capacity part CP1 are bonded to each other by an adhesive ADH2. For example, in the present embodiment 1, the sensor module SM mounted onto the back surface (lower surface) of the wiring board WB1, and the bottom face of the capacity part CP1 are adhered by a double side adhesive tape. Thus, the sensor included in the sensor module SM is fixed to the capacity part CP1, and thus the module unit MJU1 is fixed to the capacity part CP1.

Thus, according to the eighth feature point in the present embodiment 1, it is possible to suppress the rattling of the module unit MJU1. Further, when the acceleration sensor is used as the sensor included in the sensor module SM, it is possible to suppress superimposition of noise on the acceleration sensor due to the rattling. Consequently, degradation in sensing sensitivity of the acceleration sensor can be suppressed. That is, the rattling of the module unit MJU1 is suppressed by the eighth feature point in the present embodiment 1, so that the acceleration sensor is made integral with the case CS, by extension, the object animal to make the same movements. From this point, according to the electronic apparatus EA1 according to the present embodiment 1, the original performance (sensing sensitivity) of the acceleration sensor can be derived. This means that it is possible to acquire data on which the motion of the object animal is faithfully reflected. It can be said that the eighth feature point in the present embodiment 1 contributes even to acquiring significant data accurately corresponding to the behavior and state of the object animal through the fact that the rattling of the module unit MJU1 is suppressed.

Incidentally, as the adhesive ADH2, wax or a visible curing type temporary fixing material can be used in addition to the above-described double side adhesive tape. For example, as the adhesive ADH2, wax of such a type that it can be peeled off by being immersed in heating water can be used.

Next, a ninth feature point in the present embodiment 1 will be described. For example, as shown in FIGS. 11A and 11B, the ninth feature point in the present embodiment 1 resides in that conductor patterns (metal patterns) and electronic parts are not arranged around the antenna ANT as much as possible. For example, in plan view, the antenna ANT is provided in a position not to overlap with the electronic parts being the components of the module unit MJU1 typified by the sensor module SM and the connector CNT. Thus, according to the present embodiment 1, the properties of the antenna ANT can be improved. As a result, the communication range of the module can be made long. That is, when each conductor pattern exists around the antenna ANT, the properties of the antenna ANT are substantially degraded due to a shielding effect of electromagnetic waves by the conductor pattern. Thus, in the present embodiment 1, the conductor patterns are not arranged around the antenna ANT as much as possible.

From the above, according to the ninth feature point in the present embodiment 1, the communication range of the electronic apparatus EA1 (node) can be made long since the properties of the antenna ANT can be improved. This means that the room for selection of the communication path of the wireless sensor network is enlarged. That is, for example, even if the communication path between the adjacent nodes is placed in a state of being not able to use due to a communication failure by an increase in the communication range of each node, it is possible to ensure the communication path between the corresponding node and the node away therefrom. Therefore, the wireless sensor network insusceptible to the communication failure can be constructed by using the electronic apparatus EA1 according to the present embodiment 1 in each node of the wireless sensor network.

Thus, according to the ninth feature point in the present embodiment 1, the communication range of the electronic apparatus EA1 can be made long by the improvement in the antenna properties. According to the ninth feature point in the present embodiment 1, this means that the electronic apparatus EA1 less susceptible to the behavioral range of the object animal can be provided. As a result, the electronic apparatus EA1 according to the present embodiment 1 can cope even with the case where the natural behavioral range of the object animal is wide. Thus, it is possible to acquire significant data corresponding to the natural behavior and state of the object animal.

Modification 1

An electronic apparatus EA2 according to the present modification 1 will subsequently be described. FIG. 21 is a diagram showing a part of the electronic apparatus EA2 according to the present modification 1 in an enlarged form. The electronic apparatus EA2 according to the present modification 1 shown in FIG. 21 is substantially similar in configuration to the electronic apparatus EA1 according to the embodiment 1 shown in FIG. 14, and points of difference therebetween will therefore be mainly explained.

In FIG. 21, in the electronic apparatus EA2 according to the present modification 1, the case CS itself is formed of an industrial silicone resin and the surface of the case CS is coated with a coating film CAT comprised of a biocompatible silicon resin. Thus, it is possible to obtain advantages shown below.

For example, since the electronic apparatus EA1 according to the embodiment 1 shown in FIG. 14 is premised on the fact that it is implanted in the object animal, the case CS itself is formed of the biocompatible silicon resin. Thus, according to the electronic apparatus EA1 according to the embodiment 1, it is possible to reduce damage to the in-body tissue of the object animal.

Since, however, the biocompatible material is required to satisfy a high quality management standard, there is a demerit that the unit price of the material is high and the manufacturing cost of the electronic apparatus EA1 rises. Thus, the present modification 1 adopts a configuration in which the case CS itself is formed of an industrial silicone resin and the surface of the case CS is coated with a coating film CAT comprised of a biocompatible silicone resin.

Here, the industrial silicone resin is lower even in quality management standard and relatively more inexpensive than the biocompatible silicone resin. Thus, according to the electronic apparatus EA2 according to the present modification 1, since the case CS itself is formed of the industrial silicone resin more inexpensive than the biocompatible silicone resin, the manufacturing cost of the electronic apparatus EA2 can be reduced.

When, however, the case CS formed of the industrial silicone resin is implanted in the object animal, it exerts an adverse effect on the in-body tissue of the object animal. This imparts extremely large stress to the object animal. This exerts an adverse effect even on the health of the object animal rather than a difficulty in acquiring significant data corresponding to the natural behavior and state of the object animal.

Thus, in the present modification 1, the case CS itself is formed of the inexpensive industrial silicone resin, and the surface of the case CS is coated with the coating film CAT comprised of the biocompatible silicone resin. In this case, even if the case CS is implanted in the object animal, the coating film CAT comprised of the biocompatible silicone resin rather than the industrial silicone resin directly contacts the in-body tissue of the object animal. Therefore, it is possible to reduce damage to the in-body tissue of the object animal. Thus, according to the electronic apparatus EA2 according to the present modification 1, the coating film CAT comprised of the biocompatible silicone resin is formed while reducing the manufacturing cost of the electronic apparatus EA2 by using the industrial silicone resin as the material for the case CS itself. It is therefore possible to reduce stress applied to the object animal in which the electronic apparatus EA2 is implanted.

Incidentally, the coating film CAT comprised of the biocompatible silicone resin can be formed by, for example, a dipping method. At this time, when it is not possible to form a coating film CAT having a required film thickness at one dipping, the thickness of the coating film CAT can be ensured by carrying out a plurality of times of dippings.

Modification 2

Figure 22:
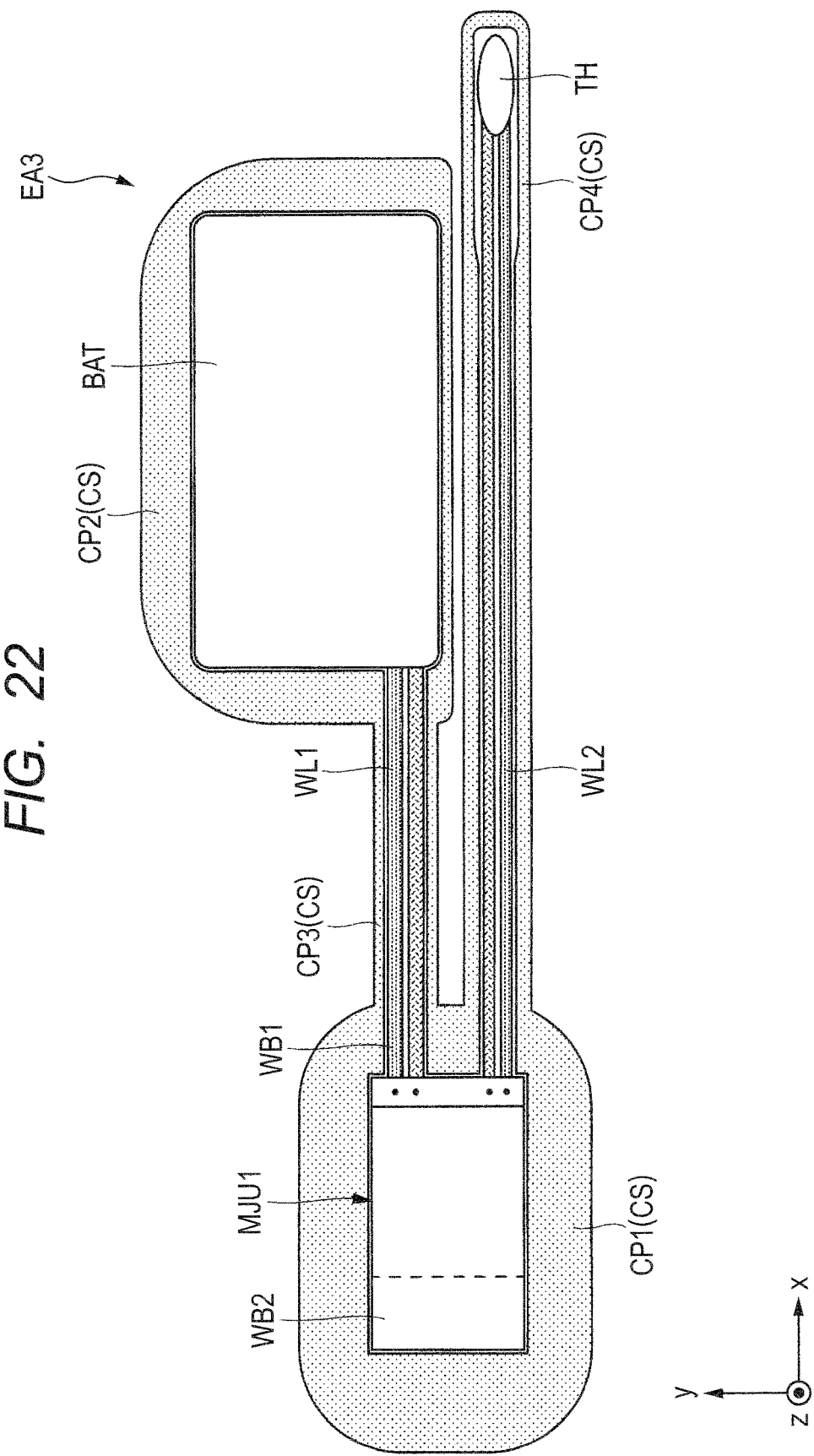
FIG. 22 is a transparent plan diagram showing a typical mounting structure of an electronic apparatus according to a modification 2.

An electronic apparatus EA3 according to the present modification 2 will next be described. FIG. 22 is a transparent plan diagram showing a typical mounting structure of the electronic apparatus EA3 according to the present modification 2. In FIG. 22, the feature point of the electronic apparatus EA3 according to the present modification 2 resides in that, for example, the corners of the capacity part CP1 configuring a part of the case CS are respectively formed in a curved shape (round shape), and the corners of the capacity part CP2 are also respectively formed in a curved shape (round shape). Thus, when the electronic apparatus EA3 according to the present modification 2 is implanted in the body of the object animal, damage to the in-body tissue of the object animal can be reduced by the above-described round shape. Further, this damage reduction means that it is possible to reduce stress given to the object animal only by this reduction. Consequently, the natural behavior and state of the object animal are easily maintained. As a result, according to the electronic apparatus EA3 according to the present modification 2, there can be obtained an advantage that it becomes easy to acquire significant data corresponding to the natural behavior and state of the object animal.

Figure 23:
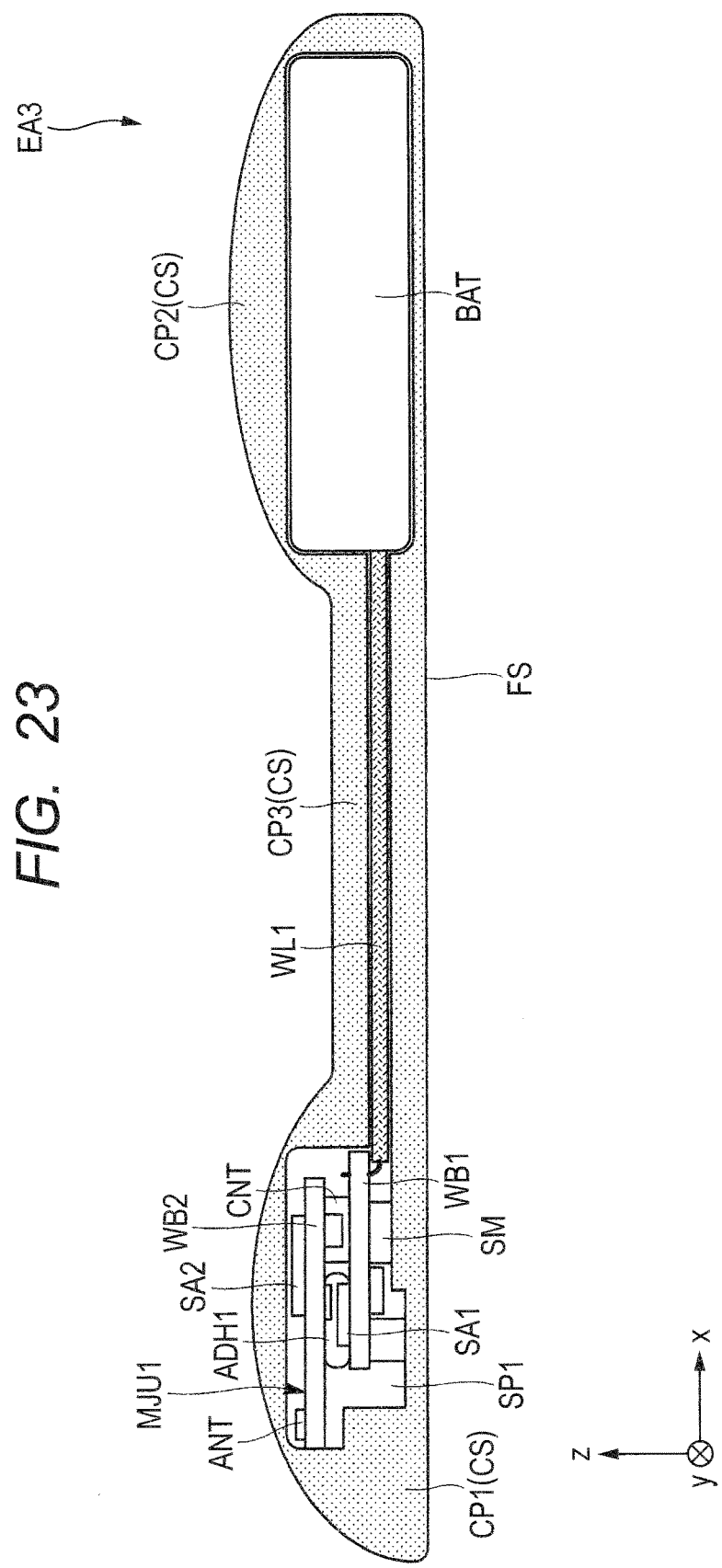
FIG. 23 is a transparent side diagram showing the typical mounting structure of the electronic apparatus according to the modification 2.

Further, FIG. 23 is a transparent side diagram showing the typical mounting structure of the electronic apparatus EA3 according to the modification 2. In FIG. 23, the feature point of the electronic apparatus EA3 according to the present modification 2 resides in that a flat surface FS is formed in the case CS over the capacity parts CP1, CP2 and CP3 (coupling part). Thus, there can be obtained an advantage that the electronic apparatus EA3 becomes easy to be implanted in the object animal. For example, it is considered that the electronic apparatus EA3 is implanted along the bone of the object animal. In this case, in the electronic apparatus EA3 according to the present modification 2, the electronic apparatus EA3 can be implanted in the body of the object animal without giving a sense of incompatibility to the object animal by allowing the flat surface FS to contact along the bone of the object animal.

From the above, according to the electronic apparatus EA3 according to the present modification 2, the damage to the in-body tissue of the object animal can be reduced by forming the corners of the case CS in the round shape, and the electronic apparatus EA3 can be implanted in the body of the object animal without giving the sense of incompatibility to the object animal by taking the bottom face of the case CS to be the flat surface FS.

Incidentally, in the present modification 2, as shown in FIG. 23, for example, the wiring WL1 is coupled to the wiring board WB1 from the lower side of the wiring board WB1. Similarly, although not shown in FIG. 23, the wiring WL2 is also coupled to the wiring board WB1 from the lower side of the wiring board WB1.

Modification 3

Figure 24:
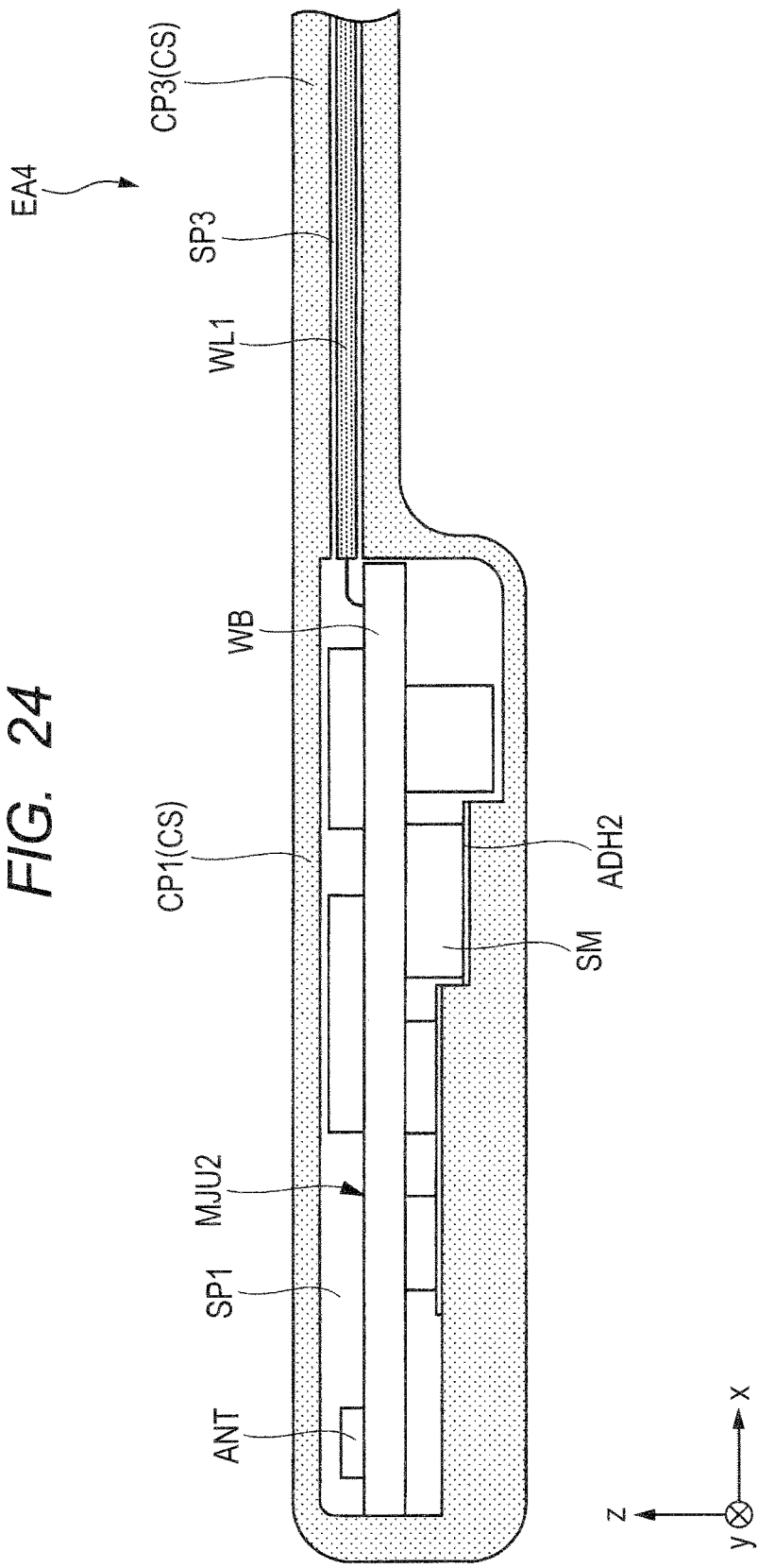
FIG. 24 is a diagram showing a part of an electronic apparatus according to a modification 3 in an enlarged form.

A description will subsequently be made about an electronic apparatus EA4 according to the present modification 3. FIG. 24 is a diagram showing a part of the electronic apparatus EA4 according to the present modification 3 in an enlarged form. The feature of the electronic apparatus EA4 according to the present modification 3 shown in FIG. 24 resides in that a module unit MJU2 has one wiring board WB, and electronic parts configuring the module unit MJU2 are mounted over both surfaces of the wiring board WB. That is, the module unit MJU1 in the embodiment 1 shown in FIG. 14 is comprised of the laminated structure of the wiring board WB1 mounted with the electronic parts, and the wiring board WB2 mounted with the electronic parts. On the other hand, the module unit MJU2 in the present modification 3 shown in FIG. 24 is comprised of the wiring board WB mounted with the electronic parts, but does not take the laminated structure.

In this case, according to the present modification 3, while the flat area (footprint) of the module unit MJU2 increases, the module unit MJU2 can be made thin. Thus, according to the electronic apparatus EA4 according to the present modification 3, the object animal is hard to feel stress even if the electronic apparatus EA4 is implanted in the object animal, and the natural behavior and state of the object animal are held. Therefore, there can be obtained a remarkable effect that effective and significant data about the object animal can be acquired by adopting the electronic apparatus EA4 according to the present modification 3 for each node of the wireless sensor network.

<Manufacturing Method of Electronic Apparatus>

Figure 25:
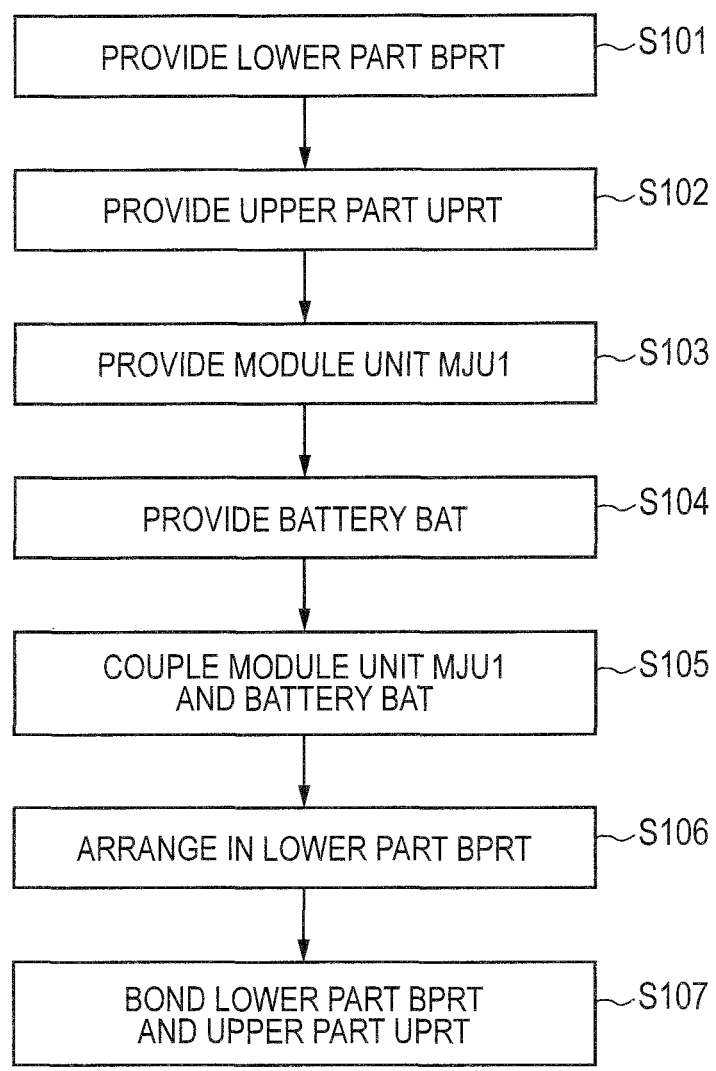
FIG. 25 is a flowchart showing the flow of a manufacturing process of the electronic apparatus according to the embodiment 1.

A method for manufacturing the electronic apparatus EA1 according to the present embodiment 1 will next be described with reference to the drawings. FIG. 25 is a flowchart showing the flow of a manufacturing process of the electronic apparatus EA1 according to the present embodiment 1.

Figure 26:
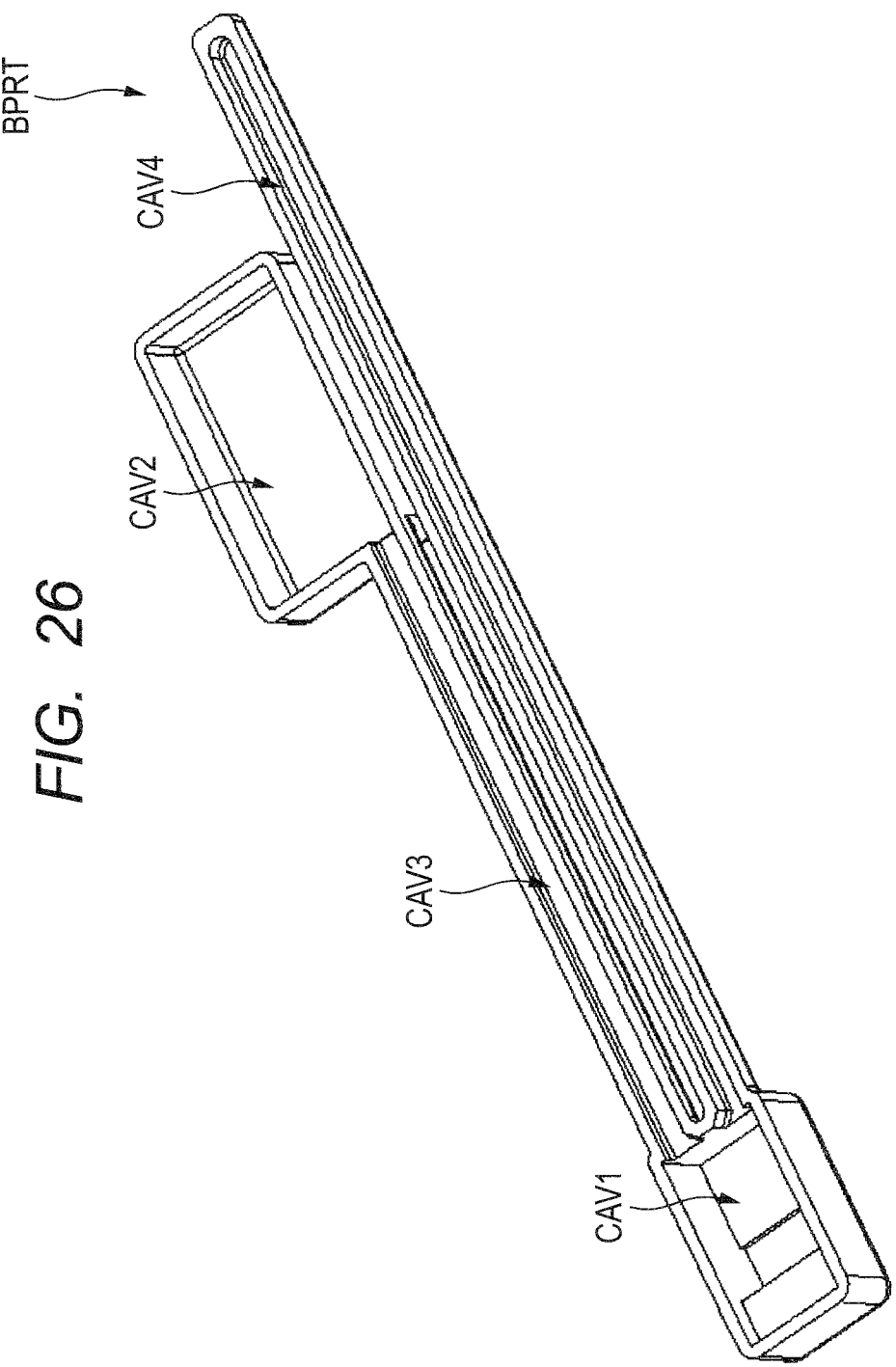
FIG. 26 is a perspective diagram typically showing the configuration and shape of a lower part.

A lower part BPRT which becomes a part of a case is first provided (S101). Specifically, FIG. 26 is a perspective diagram typically showing the configuration and shape of the lower part BPRT. As shown in FIG. 26, the provided lower part BPRT is formed with a concave portion CAV1, a concave portion CAV2 spaced away from the concave portion CAV1, a concave portion CAV3 which couples the concave portion CAV1 and the concave portion CAV2, and a concave portion CAV4 coupled to the concave portion CAV1. Incidentally, although not shown in FIG. 26, the lower part BPRT is formed with, for example, the projection part PJ1 and the projection part PJ2 shown in FIGS. 17 and 19.

Figure 27:
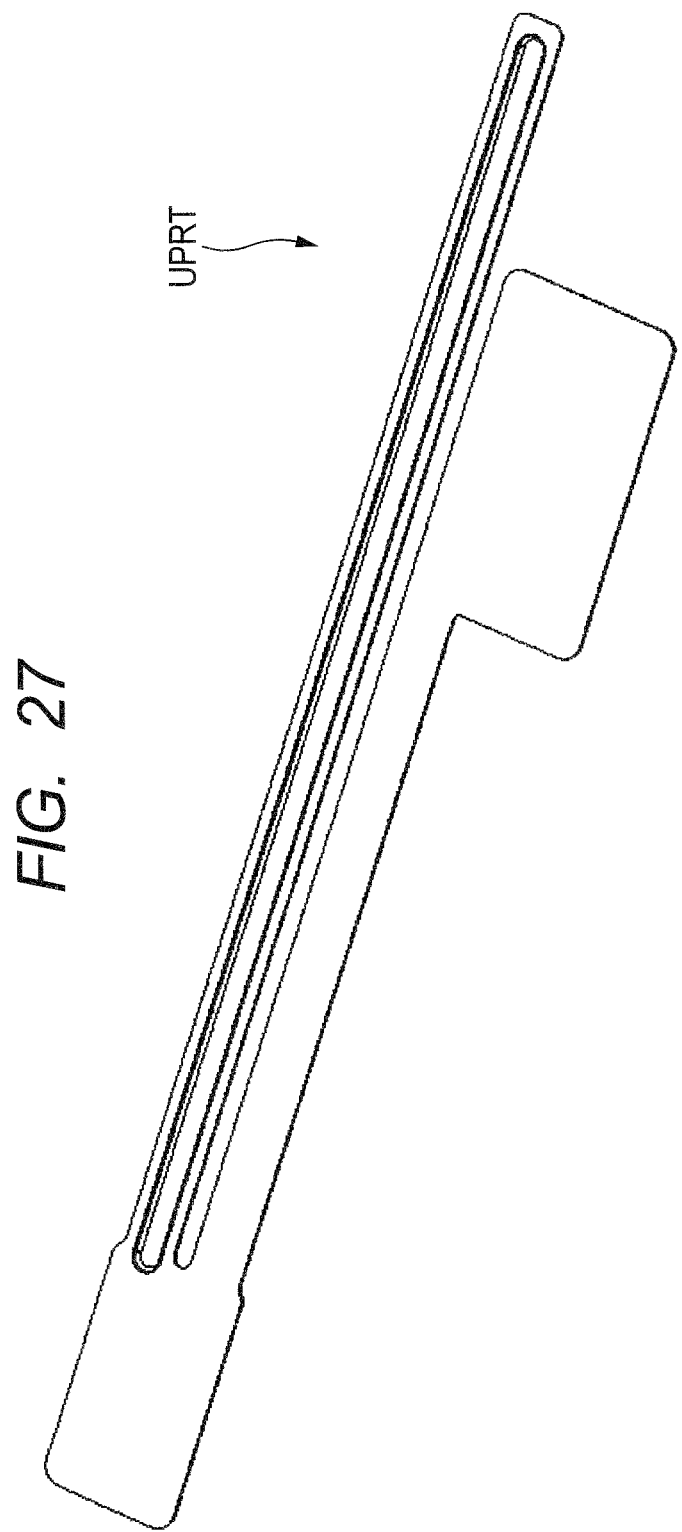
FIG. 27 is a perspective diagram typically showing the configuration and shape of an upper part.

Also, an upper part UPRT which becomes apart of the case is provided (S102). Specifically, FIG. 27 is a perspective diagram typically showing the configuration and shape of the upper part UPRT. The upper part UPRT shown in FIG. 27 has the function of sealing the concave portion CAV1, the concave portion CAV2, the concave portion CAV3, and the concave portion CAV4 formed in the lower part BPRT.

Further, a module unit MJU1 is provided (S103). Specifically, the module unit MJU1 is provided which has a sensor which detects a physical quantity typified by acceleration, and a radio communication unit which transmits data based on an output signal from the sensor. For example, the module unit MJU1 in the present embodiment 1 has the wiring board WB1 shown in FIG. 9, and the wiring board WB2 shown in FIG. 10. These wiring boards WB1 and WB2 are laminated over each other as shown in FIGS. 11A and 11B. That is, as shown in FIG. 11B, the adhesive (silicone adhesive) ADH1 is supplied to predetermined positions of the wiring board WB1 and the wiring board WB2, and the connector CNT is fitted therein, followed by execution of a cure process (120° C. and 1 hour), whereby the module unit MJU1 comprised of the laminated structure of the wiring board WB1 and the wiring board WB2 is provided.

Then, for example, a battery BAT comprised of a lithium ion battery is also provided (S104). At this time, a battery BAT to which wirings are coupled in advance may be provided. This battery BAT has the function of supplying power to the module unit MJU1.

Figure 28:
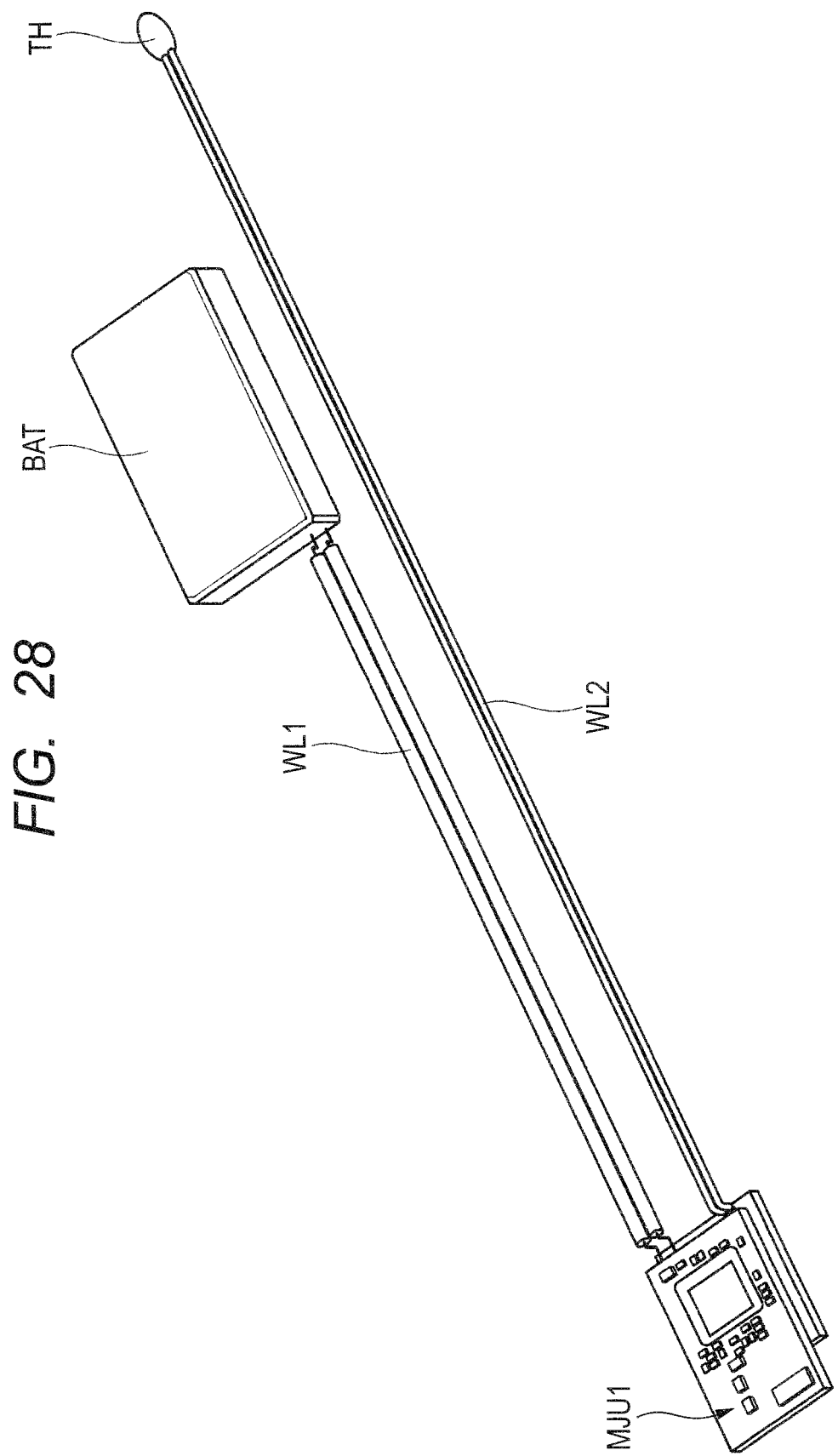
FIG. 28 is a perspective diagram typically showing a state in which a module unit and a battery are coupled by wirings, and the module unit and a thermistor are coupled by wirings.

Subsequently, for example, the module unit MJU1 and the battery BAT are coupled by a wiring WL1 using solder coupling (S105). Specifically, as shown in FIG. 28, the module unit MJU1 and the battery BAT are coupled by the wiring WL1, and the module unit MJU1 and a thermistor TH being a temperature sensor are electrically coupled using a wiring WL2 coupled to the thermistor TH in advance. Further, a double-sided tape is adhered to at least a region of the module unit MJU1 including the back surface of a sensor module. Incidentally, the double-sided tape may be attached even to the back surface of the battery BAT.

Next, pretreatment for molecular adhesion of the upper part UPRT and the lower part BPRT is carried out. Specifically, the upper part UPRT and the lower part BPRT are set to a jig. After the upper part UPRT and the lower part BPRT are supported not to deform, corona discharge treatment corresponding to the pretreatment is carried out.

Figure 29:
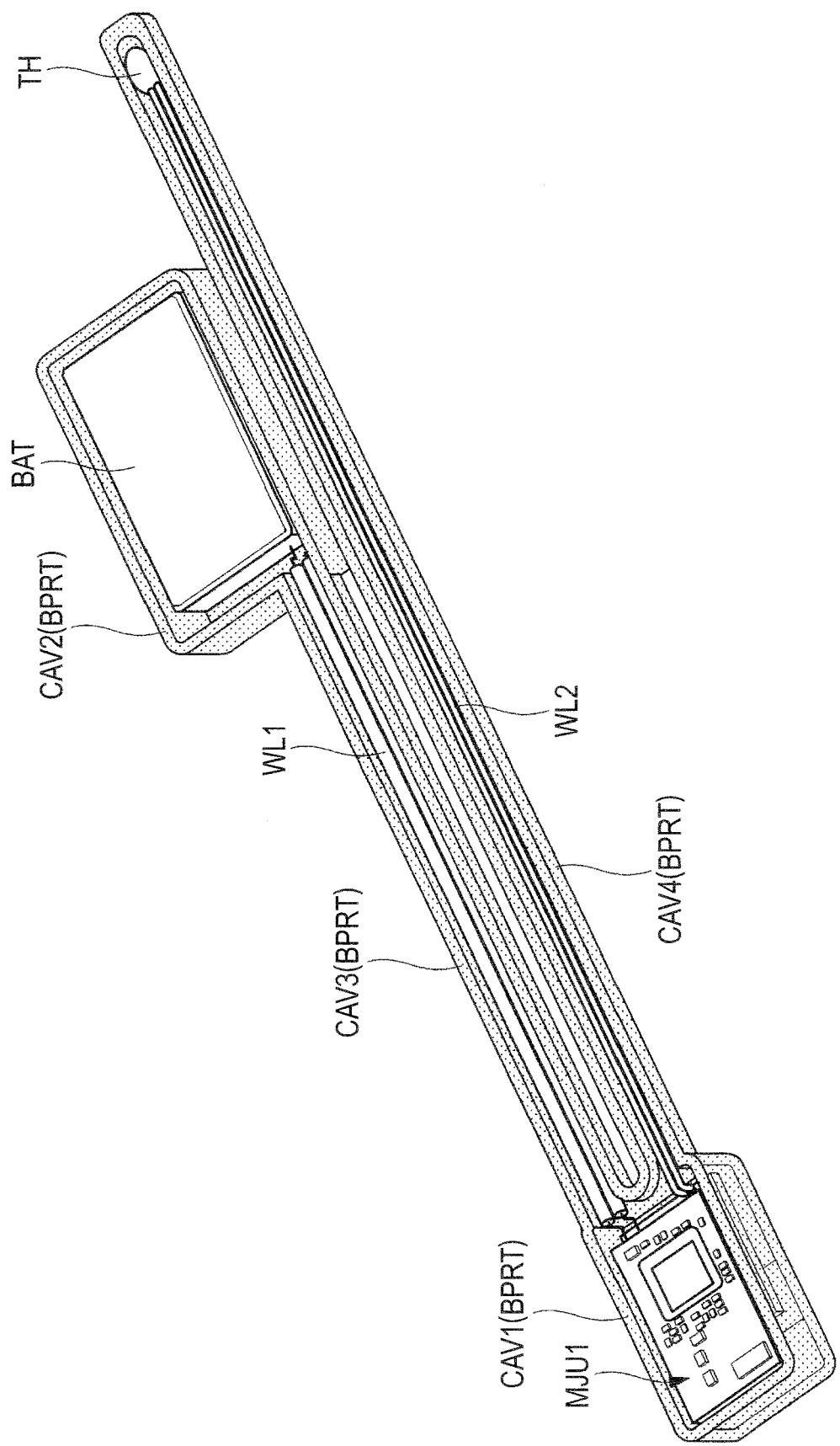
FIG. 29 is a perspective diagram typically showing a state in which the module unit, battery and thermistor integrated with each other are arranged in the lower part.

Thereafter, the integrated module unit MJU1, battery BAT and thermistor TH are arranged within the lower part BPRT (S106). Specifically, as shown in FIG. 29, the module unit MJU1 is arranged in the concave portion CAV1 of the lower part BPRT, an the battery BAT is arranged in the concave portion CAV2 of the lower part BPRT. Here, the module unit MJU1 is fixed to the bottom face of the concave portion CAV1 by the double sided tape. Also, the battery BAT is fixed to the bottom face of the concave portion CAV2 by the double sided tape. Further, the wiring WL1 is arranged in the concave portion CAV3 of the lower part BPRT, and the wiring WL2 is arranged in the concave portion CAV4 of the lower part BPRT.

At this time, according to the fourth and sixth feature points in the present embodiment 1 described above, the wiring WL1 becomes easy to be accommodated in the concave portion CAV3 of the lower part BPRT, and a part of the wiring WL1 can be suppressed from protruding from the lower part BPRT. Similarly, the wiring WL2 becomes easy to be accommodated in the concave portion CAV4 of the lower part BPRT, and a part of the wiring WL2 can be suppressed from protruding from the lower part BPRT.

Subsequently, the concave portion CAV1, the concave portion CAV2, the concave portion CAV3, and the concave portion CAV4 are sealed by adhering the lower part BPRT and the upper part UPRT to each other (S107). Specifically, the upper part UPRT is aligned in position to contact the lower part BPRT, followed by execution of a heating/pressing process, whereby the molecular adhesion of the upper part UPRT and the lower part BPRT is completed. This heating/pressing process is carried out under the conditions of, for example, 60° C. (temperature), 5 kgf (load) and 30 minutes (time). When the temperature is high, the adhesion is possible for a short period of time, but the temperature is set to 60° C. in consideration of heat resistance of the battery BAT.

Figure 30:
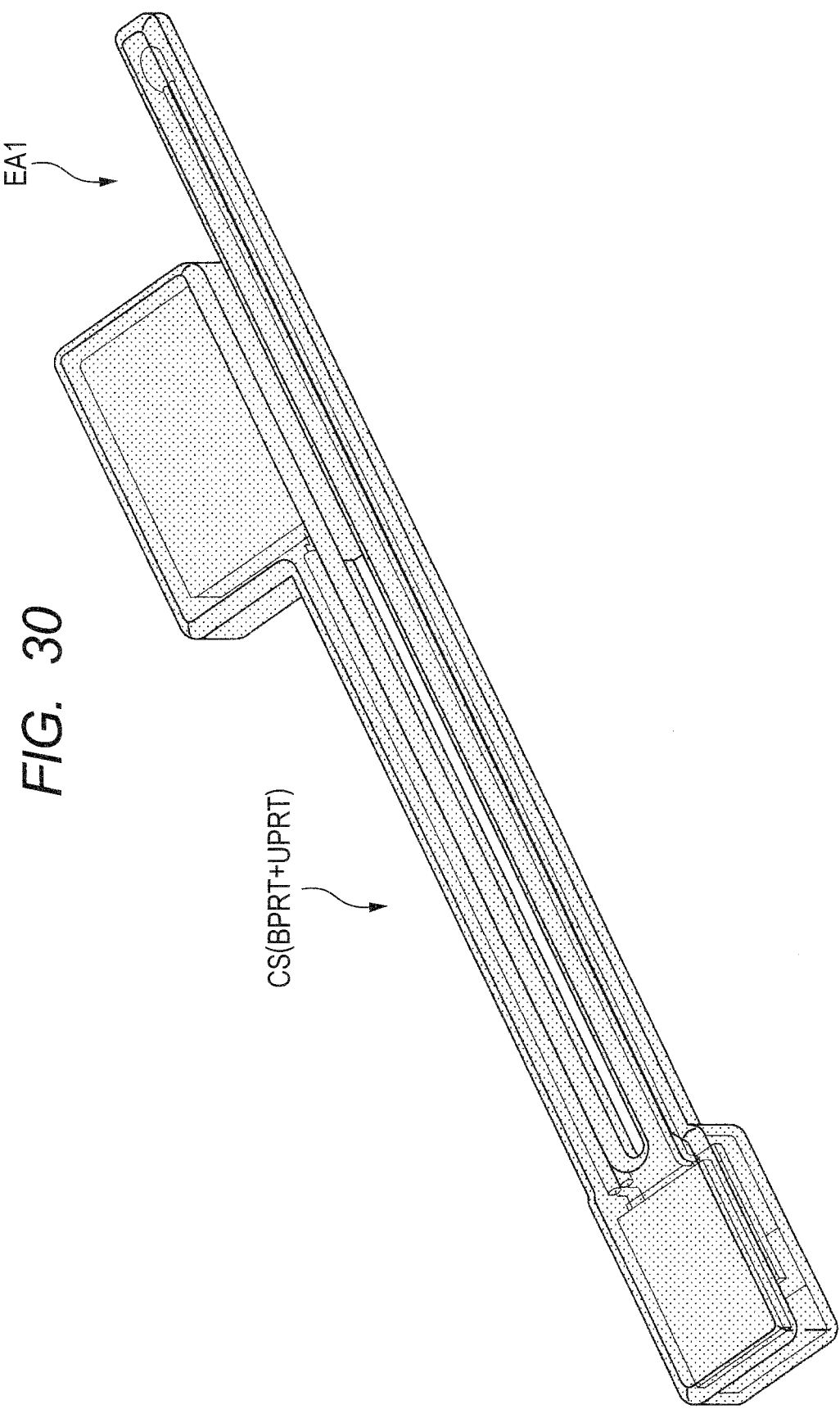
FIG. 30 is a perspective diagram typically showing the electronic apparatus according to the embodiment 1.

In the above-described manner, the electronic apparatus EA1 according to the present embodiment 1 sealed by the case CS can be manufactured as shown in FIG. 30.

Incidentally, in the present embodiment 1, the method for the adhesion of the upper part UPRT and the lower part BPRT has used the molecular adhesion method, but is not limited to it. An adhesive can also be used, or an intermolecular force adhesion method can also be used.

Embodiment 2

<Mounting Structure of Electronic Apparatus>

A description will next be made about an electronic apparatus EA5 according to the present embodiment 2.

Figure 31:
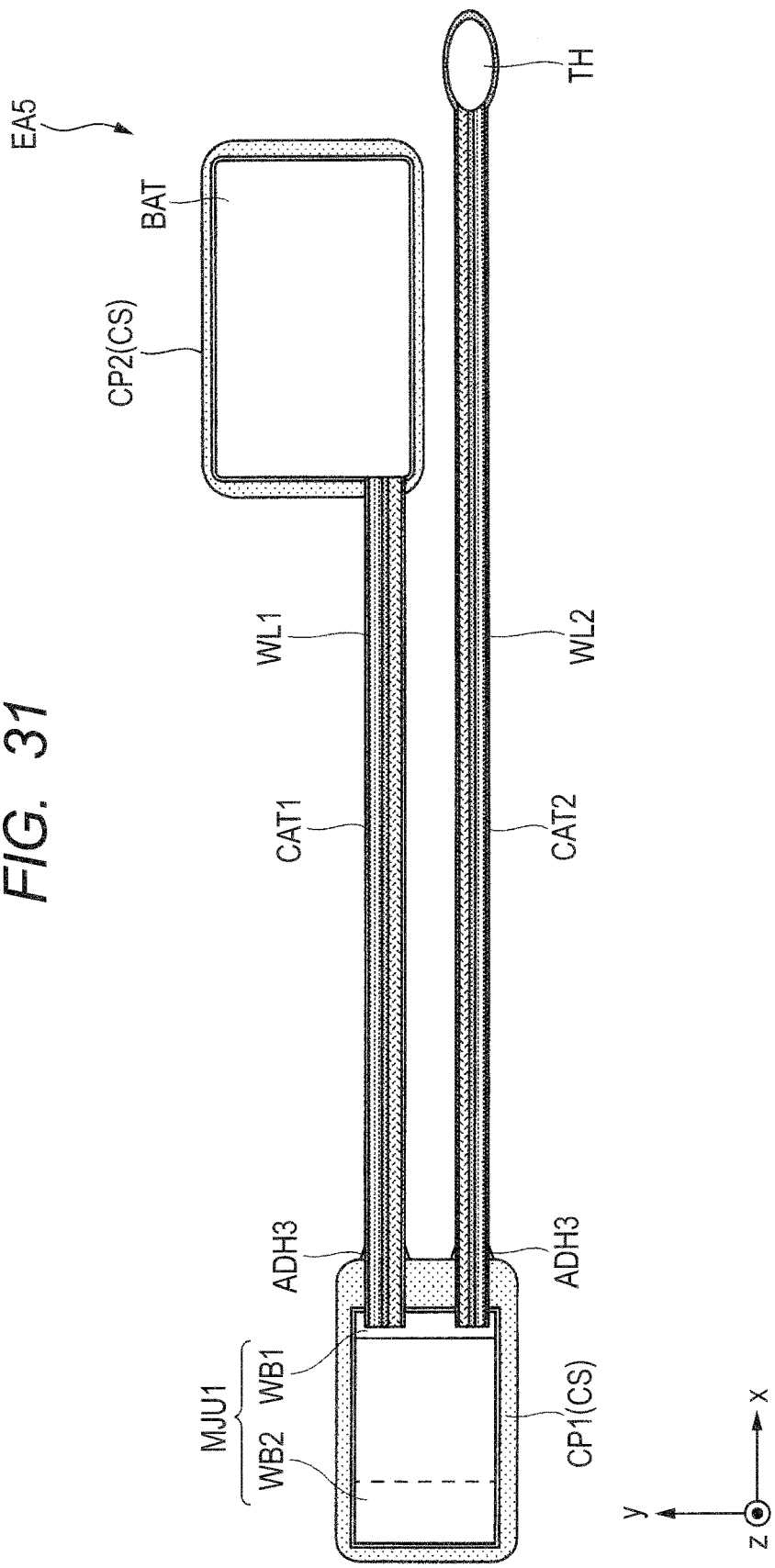
FIG. 31 is a transparent plan diagram showing a typical mounting structure of an electronic apparatus according to an embodiment 2.

FIG. 31 is a transparent plan diagram showing a typical mounting structure of the electronic apparatus EA5 according to the present embodiment 2. Also, FIG. 32 is a transparent side diagram showing the typical mounting structure of the electronic apparatus EA5 according to the present embodiment 2.

Figure 32:
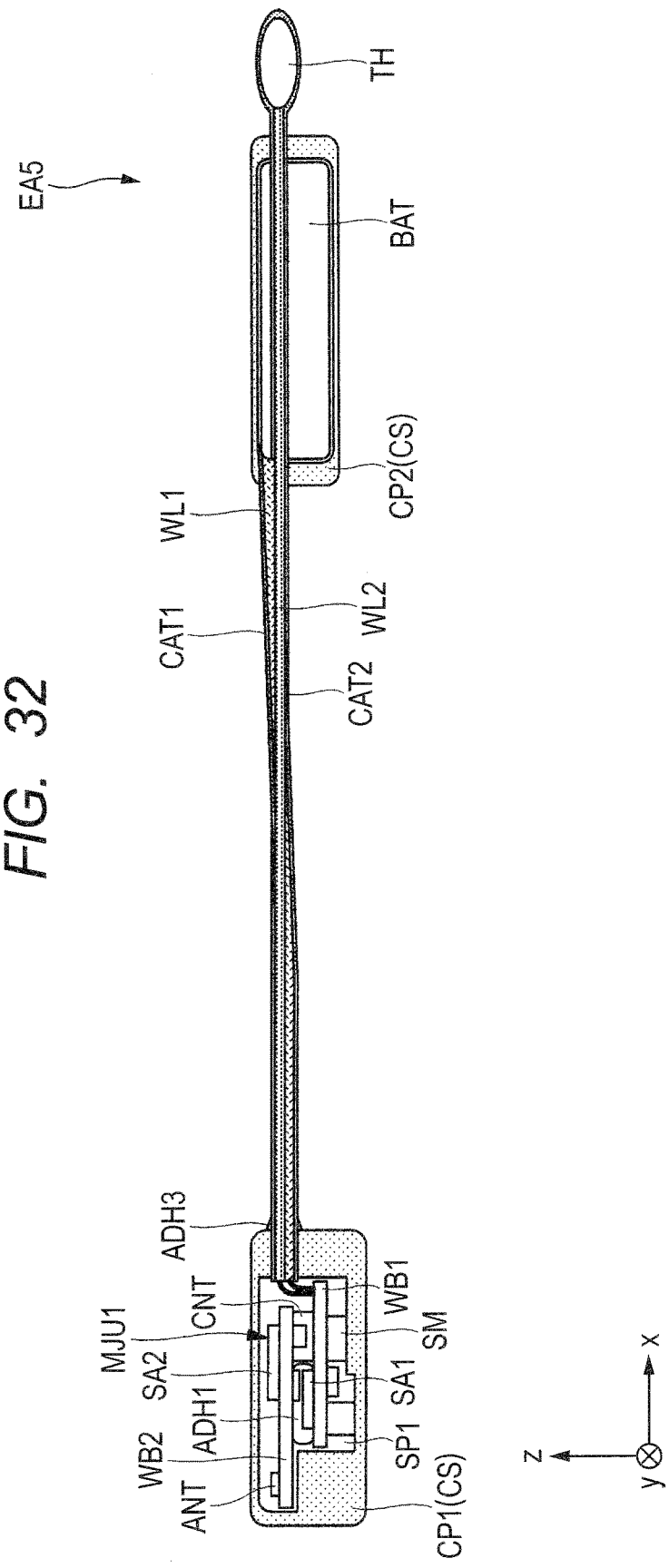
FIG. 32 is a transparent side diagram showing the typical mounting structure of the electronic apparatus according to the embodiment 2.

In FIGS. 31 and 32, the feature point of the present embodiment 2 resides in that a coupling part for electrically coupling a module unit MJU1 accommodated in a capacity part CP1 comprised of a biocompatible material and a battery BAT accommodated in a capacity part CP2 comprised of a biocompatible material is formed of a wiring WL1 coated with a coating film CAT1 comprised of a biocompatible material.

Thus, according to the electronic apparatus EA5 according to the present embodiment 2, it is possible to improve flexibility of the coupling part. This means that the coupling part of the electronic apparatus EA5 becomes easy to deform following the movement of an object animal in which the electronic apparatus EA5 according to the present embodiment 2 is implanted. Thus, the object animal becomes hard to feel stress, and the natural behavior and state of the object animal are held. Therefore, there can be obtained a remarkable effect that effective and significant data about the object animal can be acquired by adopting the electronic apparatus EA5 according to the present embodiment 2 in each node of the wireless sensor network.

Incidentally, in the electronic apparatus EA5 according to the present embodiment 2, a reinforcing adhesive ADH3 formed of a biocompatible material is provided at a coupling part of the capacity part CP1 and the wiring WL1 in order to improve the strength of the coupling part of the capacity part CP1 and the wiring WL1.

In FIGS. 31 and 32, a thermistor TH electrically coupled to the module unit MJU1 accommodated in the capacity part CP1 comprised of the biocompatible material via a wiring WL2 is coated with a coating film CAT2 comprised of a biocompatible material, and the wiring WL2 is also coated with the coating film CAT2 comprised of the biocompatible material. At this time, according to the electronic apparatus EA5 according to the present embodiment 2, a reduction in the temperature detection sensitivity of the thermistor TH can be suppressed because the thickness of the coating film CAT2 for coating the thermistor TH becomes thin.

Incidentally, in the electronic apparatus EA5 according to the present embodiment 2, a reinforcing adhesive ADH3 formed of a biocompatible material is provided at a coupling part of the capacity part CP1 and the wiring WL2 in order to improve the strength of the coupling part of the capacity part CP1 and the wiring WL2.

<Manufacturing Method of Electronic Apparatus>

Figure 33:
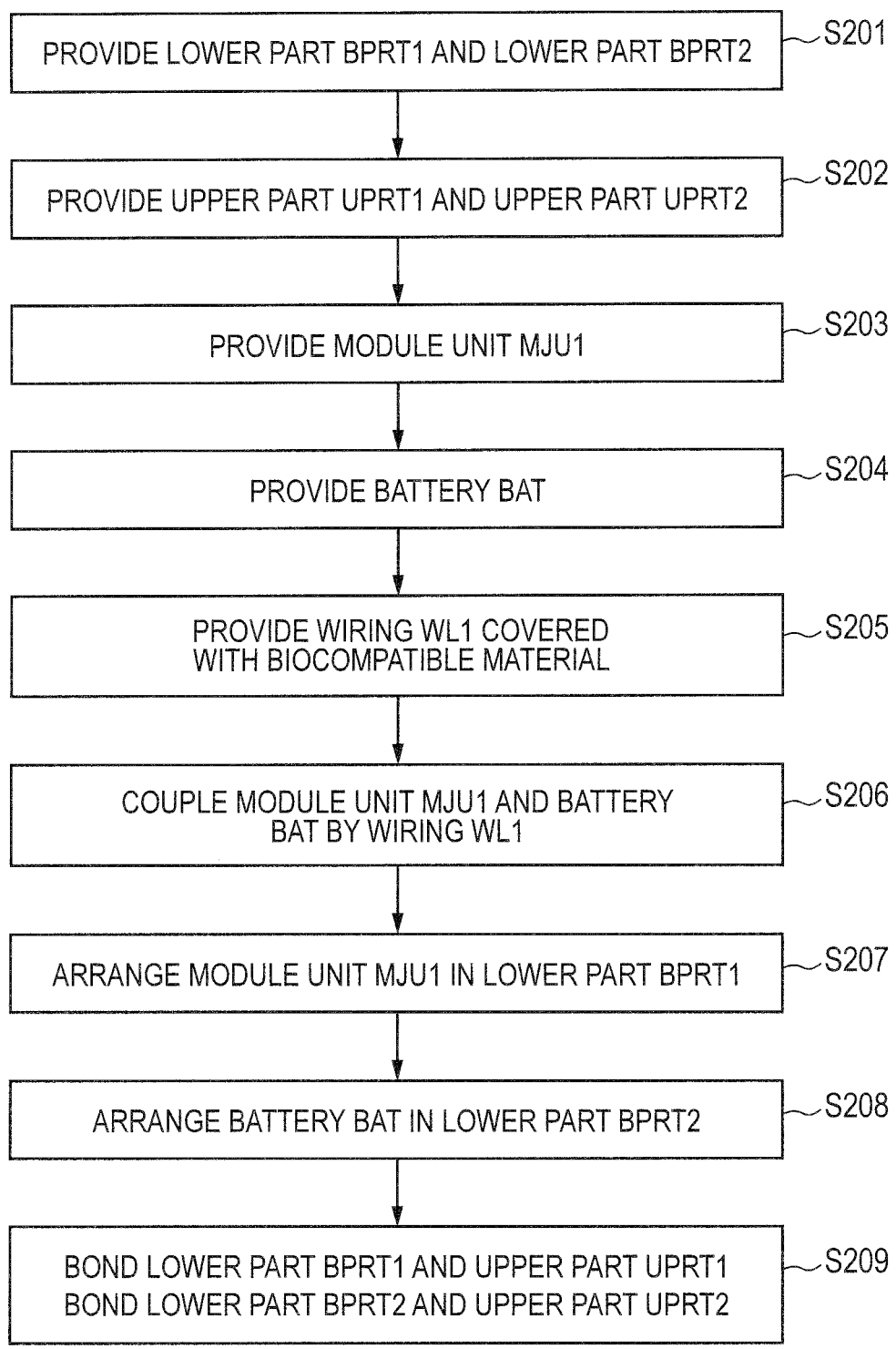
FIG. 33 is a flowchart showing the flow of a manufacturing process of the electronic apparatus according to the embodiment 2.

A method for manufacturing the electronic apparatus EA5 according to the present embodiment 2 will subsequently be described. FIG. 33 is a flowchart showing the flow of a manufacturing process of the electronic apparatus EA5 according to the present embodiment 2. In FIG. 33, a lower part BPRT1 formed with a first concave portion, and a lower part BPRT2 formed with a second concave portion are first provided (S201). Further, an upper part UPRT1 for sealing the first concave portion of the lower part BPRT1, and an upper part UPRT2 for sealing the second concave portion of the lower part BPRT2 are provided (S202).

Further, a module unit MJU1 having a sensor which detects a physical quantity and a radio communication unit which transmits data based on an output signal from the sensor, is provided (S203). Besides, a battery BAT for supplying power to the module unit MJU1 is provided (S204).

Next, a wiring WL1 coated with a biocompatible material, and a thermistor (including a wiring) coated with a biocompatible material are provided (S205). Specifically, the wiring WL1 and the thermistor are formed with a coating film at their surfaces by executing dipping—drying (ambient temperature)—calcination (80° C., 1 hr.) on the biocompatible material after their ends to be bonded with solder later are masked with a tape or the like. At this time, since the wiring WL1 and the thermistor have no structural portion to be taken as a blind and are relatively smooth at their surfaces, the occurrence of voids due to the entrainment of bubbles at dipping can be avoided relatively easily, and the detection of the presence or absence of the voids is also relatively easy. Further, since the coating film can be formed separately from the battery BAT and the module unit MJU1, calcination at a relatively high temperature is also applicable and work efficiency can be improved. On the other hand, when the module unit is coupled to the battery BAT, an improvement in the work efficiency becomes hard to be realized because there exists a restriction on the maximum temperature 60° C. from the need to ensure heat resistance of the battery BAT.

Incidentally, since the wiring WL1 and the thermistor are smooth and relatively simple in shape where the thickness of the coating film is made thick, dipping to a high viscosity resin is applicable by an adjustment in the content of a solvent. This dipping enables an increase in the thickness of the coating film. As another means for attaining the increase in the thickness of the coating film, the increase in the thickness of the coating film can be realized by repeating a plurality of cycles with a series of processes of dipping-drying-calcination as one cycle.

Subsequently, the module unit MJU1 and the battery BAT are coupled by the wiring WL1 coated with the coating film, and the module unit MJU1 and the thermistor (including the wiring) are electrically coupled (S206).

Thereafter, the module unit MJU1 is arranged in the lower part BPRT1 (S207), and the battery BAT is arranged in the lower part BPRT2 (S208). Further, the lower part BPRT1 and the upper part UPRT1 are bonded to each other, and the lower part BPRT2 and the upper part UPRT2 are bonded to each other (S209). Specifically, the molecular adhesion method is used as with the embodiment 1 even in the present embodiment 2. In the present embodiment 2, however, the module unit MJU1 and the battery BAT are hermetically sealed by the separate parts. Thus, as shown in FIGS. 31 and 32, the capacity part CP1 comprised of the sealing structure of the lower part BPRT1 and the upper part UPRT1, and the capacity part CP2 comprised of the sealing structure of the lower part BPRT2 and the upper part UPRT2 are formed. At this time, as shown in FIGS. 31 and 32, the capacity part CP1 and the capacity part CP2 are coupled by the coupling part comprised of the wiring WL1 coated with the biocompatible material, and the capacity part CP1 and the thermistor TH coated with the biocompatible material are coupled by the wiring WL2 coated with the biocompatible material.

At last, as shown in FIGS. 31 and 32, an adhesive ADH3 for reinforcement is formed at the coupling part of the capacity part CP1 and the wiring WL1 and the coupling part of the capacity part CP1 and the wiring WL2. Thus, it is possible to improve the mechanical strength of each of the coupling part of the capacity part CP1 and the wiring WL1 and the coupling part of the capacity part CP1 and the wiring WL2. Incidentally, the reinforcing adhesive ADH3 is formed of a biocompatible material.

The electronic apparatus EA5 according to the present embodiment 2 can be manufactured in the above-described manner.

Although the invention made above by the present inventors has been described specifically on the basis of the preferred embodiments, the present invention is not limited to the embodiments referred to above. It is needless to say that various changes can be made thereto within the scope not departing from the gist thereof.

What is claimed is:

1. An electronic apparatus functioning as a component of a wireless communication system, the electronic apparatus comprising:
   a sealed case including:
      a first capacity part including a first space;
      a second capacity part, in a plan view, provided away from the first capacity part and including a second space;
      a coupling part which couples the first capacity part and the second capacity part,
         the electronic apparatus including a module unit accommodated in the first space of the first capacity part, and a battery accommodated in the second space of the second capacity part,
         the coupling part including a wiring which electrically couples the module unit and the battery, and
         the module unit including a sensor which detects a physical quantity, and a radio communication unit which transmits data based on an output signal from the sensor; and
      a temperature sensor electrically coupled to the module unit, in the plan view, the temperature sensor being located outside of the first capacity part, the second capacity part, and the coupling part.

2. The electronic apparatus according to claim 1, wherein the case comprises a biocompatible material.

3. The electronic apparatus according to claim 2, wherein the first capacity part and the second capacity part respectively comprise a biocompatible material, and
   wherein the coupling part comprises the wiring coated with a biocompatible material.

4. The electronic apparatus according to claim 3, wherein a reinforcing adhesive comprising a biocompatible material is provided at a coupling part of the first capacity part and the coupling part.

5. The electronic apparatus according to claim 2, wherein the first capacity part and the second capacity part respectively comprise a biocompatible material,
   wherein the coupling part includes a third capacity part including a third space,
   wherein the third capacity part comprises a biocompatible material, and
   wherein the wiring is accommodated in the third space of the third capacity part.

6. The electronic apparatus according to claim 5, wherein the third capacity part is provided with a pair of projection parts which projects toward the third space relative to each other, and
   wherein the wiring is sandwiched by the pair of projection parts.

7. The electronic apparatus according to claim 5, wherein a curved shape is formed at a coupling part of the first capacity part and the third capacity part.

8. The electronic apparatus according to claim 1, wherein a coating film comprising a biocompatible material is formed over a surface of the case.

9. The electronic apparatus according to claim 1, wherein the sensor which detects the physical quantity is fixed to the first capacity part.

10. The electronic apparatus according to claim 1, further including an antenna unit, wherein the antenna unit is provided at a position not to overlap with the sensor which detects the physical quantity in the plan view.

11. The electronic apparatus according to claim 1, wherein the case includes a flat surface which is flat over the first capacity part, the coupling part, and the second capacity part.

12. The electronic apparatus according to claim 1, wherein the sensor which detects the physical quantity includes an acceleration sensor.

13. The electronic apparatus according to claim 2, wherein the case comprises a silicone resin.

14. An electronic apparatus functioning as a component of a wireless communication system, the electronic apparatus comprising:
 a sealed case including:
  a first capacity part including a first space;
  a second capacity part provided away from the first capacity part and including a second space;
  a coupling part which couples the first capacity part and the second capacity part,
   the electronic apparatus including a module unit accommodated in the first space of the first capacity part, and a battery accommodated in the second space of the second capacity part,
   the coupling part including a wiring which electrically couples the module unit and the battery, and
   the module unit including a sensor which detects a physical quantity, and a radio communication unit which transmits data based on an output signal from the sensor; and
  a temperature sensor electrically coupled to the module unit,
 wherein the temperature sensor is coated with a biocompatible material.

15. The electronic apparatus according to claim 14, wherein a reinforcing adhesive comprising a biocompatible material is provided at a coupling part of the first capacity part and the temperature sensor.

16. An electronic apparatus functioning as a component of a wireless communication system the electronic apparatus comprising:
 a sealed case including:
  a first capacity part including a first space;
  a second capacity part provided away from the first capacity part and including a second space;
  a coupling part which couples the first capacity part and the second capacity part,
   the electronic apparatus including a module unit accommodated in the first space of the first capacity part, and a battery accommodated in the second space of the second capacity part,
   the coupling part including a wiring which electrically couples the module unit and battery, and
   the module unit including a sensor which detects a physical quantity, and a radio communication unit which transmits data based on an output signal from the sensor;
  a temperature sensor electrically coupled to the module unit; and
  a third capacity part including a third space,
 wherein the third capacity part comprises a biocompatible material, and
 wherein the temperature sensor is accommodated in the third space of the third capacity part.

17. The electronic apparatus according to claim 16, wherein the third capacity part is provided with a pair of projection parts which projects toward the fourth space relative to each other, and
 wherein the temperature sensor is sandwiched by the pair of projection parts.

18. The electronic apparatus according to claim 16, wherein a curved shape is formed at a coupling part of the first capacity part and the third capacity part.

* * * * *